US011639371B2

(12) United States Patent
Chan et al.

(10) Patent No.: US 11,639,371 B2
(45) Date of Patent: *May 2, 2023

(54) PEPTIDYLIC INHIBITORS OF NUCLEOLIN (NCL) TARGETING CAG-REPEAT RNA TOXICITY AND METHODS FOR REDUCING POLYQ-MEDIATED TOXICITY IN POLYQ DISEASES

(71) Applicant: The Chinese University of Hong Kong, Shatin (CN)

(72) Inventors: Ho Yin Edwin Chan, Hong Kong (CN); Jacky Chi-Ki Ngo, Hong Kong (CN); Qian Zhang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/046,249

(22) Filed: Feb. 17, 2016

(65) Prior Publication Data

US 2017/0233442 A1 Aug. 17, 2017

(51) Int. Cl.
| | |
|---|---|
| *A61K 38/00* | (2006.01) |
| *A61K 38/16* | (2006.01) |
| *A61K 38/18* | (2006.01) |
| *C07K 14/00* | (2006.01) |
| *C07K 14/47* | (2006.01) |
| *A61P 25/28* | (2006.01) |
| *A61K 38/17* | (2006.01) |

(52) U.S. Cl.
CPC .......... *C07K 14/47* (2013.01); *A61K 38/1709* (2013.01); *A61P 25/28* (2018.01); *A61K 38/16* (2013.01); *C07K 2319/00* (2013.01); *C07K 2319/09* (2013.01); *C07K 2319/10* (2013.01); *C07K 2319/715* (2013.01)

(58) Field of Classification Search
CPC .......... C12N 15/86; C12N 2750/14143; C12N 2750/14145; C12N 2810/50; C12N 15/1065; A61K 48/00; A61K 38/00; C07K 2319/00; C40B 50/06; C40B 40/08
See application file for complete search history.

(56) References Cited

U.S. PATENT DOCUMENTS

| | | | | |
|---|---|---|---|---|
| 8,569,065 | B2 * | 10/2013 | Polach | C12N 15/63 |
| | | | | 424/93.1 |
| 8,987,211 | B2 * | 3/2015 | Maschat | C07K 14/47 |
| | | | | 435/320.1 |
| 9,297,798 | B2 * | 3/2016 | Chan | G01N 33/6896 |
| 10,143,666 | B2 * | 12/2018 | Chan | A61K 31/155 |
| 10,570,177 | B2 * | 2/2020 | Chan | A61K 38/10 |
| 11,197,911 | B2 * | 12/2021 | Chan | A61K 45/06 |
| 2004/0005579 | A1 * | 1/2004 | Birse | C07K 14/47 |
| | | | | 435/6.14 |
| 2007/0224201 | A1 * | 9/2007 | Wu | C07K 14/47 |
| | | | | 424/155.1 |
| 2010/0233141 | A1 * | 9/2010 | Polach | C12N 15/63 |
| | | | | 424/93.7 |
| 2013/0164845 | A1 * | 6/2013 | Polach | C12N 15/111 |
| | | | | 435/375 |
| 2014/0005254 | A1 * | 1/2014 | Polach | C12N 15/63 |
| | | | | 514/44 R |
| 2014/0121167 | A1 * | 5/2014 | Maschat | C07K 14/47 |
| | | | | 514/17.7 |
| 2014/0357578 | A1 * | 12/2014 | Chan | G01N 33/6896 |
| | | | | 514/21.5 |
| 2017/0233442 | A1 * | 8/2017 | Chan | C07K 14/47 |
| | | | | 514/17.7 |
| 2018/0214515 | A1 * | 8/2018 | Chan | A61K 38/1709 |

OTHER PUBLICATIONS

Burgess et al. J of Cell Bio. 1990, 111:2129-2138.*
Pawson et al. 2003, Science 300:445-452.*
Bowie et al. Science, 1990, 247:1306-1310.*
Huntington's Disease: The voice of the patient public meeting on Sep. 22, 2015 from the FDA website: www.fda.gov/media/96350/download retrieved on Nov. 18, 2020.*
Nalavade et al.,Cell Death and Disease, 2013; 4:e752; doi:10.1038/cddis.2013.276, published online Aug. 1, 2013.*
The factsheet of Huntinig's disease from NINDS website: www.ninds.nih.gov/Disorders/Patient-Caregiver-Education/Hope-Through-Research/Huntingtons-Disease-Hope-Through retrieved on Nov. 21, 2020/.*
Clery et al. Curr. Opin. Struct. Biol. 2008; 18:290-298.*
Zhang et al. RNA, 20018; 24:486-498.*
Zhang et al. Disease Models & Mechanisms 2016; 9:321-334. doi:10.1242/dmm.022350.*
Zhang et al. PNAS, 1997; 94:4504-4509.*
Alaoui-Ismaili et al., Cytokine Growth Factor Rev. 2009; 20:501-507.*
Guo et al., PNAS 2004; 101:9205-9210.*
Zhang et al. RNA, 2018; 24:486-498.*
Zhang et al. Disease Models & Mechanisms, 2016; 9:321-334.*
Long et al. Cerebellum & Ataxia, 2014; 1:9. www.cerebellumandataxias.com/content/1/1/9.*
Ranganathan et al. Front. Neurosci. Jul. 7, 2020. doi:10.3389/fnins.2020.00684.*
Swinnen et al. The EMBO J. 2020, 39:e101112. doi: 10.1015252/embj.2018101112.*
Fiszer et al. J. Mol. Med. 2013; 91:683-691. DOI: 10.1007/s00109-013-1016-2.*
Arribat et al., "A Huntingtin Peptide Inhibits PolyQ-huntintin Associated Defects," PLOS One, Jul. 2013, vol. 8, Issue 7, 1-14.
Shaltiel-Karyo et al., "A Novel, Sensitive Assay for Behavioral Defects in Parkinson's Disease Model *Drosophila*," Hindawi Publishing Corp., Parkison's Disease, vol. 2012, Article ID 697564, 6 pages.

(Continued)

*Primary Examiner* — Chang-Yu Wang
(74) *Attorney, Agent, or Firm* — Kilpatrick Townsend & Stockton LLP

(57) ABSTRACT

The present invention provides for a novel peptide and method for treating polyglutamine (polyQ) diseases. Also disclosed are related compositions and kits for therapeutic use in the treatment of polyQ diseases.

18 Claims, 9 Drawing Sheets

Specification includes a Sequence Listing.

(56) References Cited

OTHER PUBLICATIONS

Banez-Coronel et al., "A Pathogenic Mechanism in Huntingtin's Disease involves small CAG-Repeated RNAs with Neutoxic Activity," PLoS Genetics, Feb. 2012, vol. 8, Issue 2, 1-14.

Tsoi et al., "CAG Expansion Induces Nucleolar Stress in Polyglutamine Diseases," PNAS, Aug. 14, 2012, vol. 109, No. 33, 13428-13433.

Koren et al., "Cell-Penetrating Peptides: Breaking Through to the Other Side," Trends in Molecular Medicine, Jul. 2012, vol. 18, No. 7, 385-393.

Kumar, et al., Chemical Correction of Pre-mNRA Splicing Defects Associated with Sequestrian of Muscleblind-like 1 Protein by Expanded r(CAG)-Containing Transcripts, ACS Chem Biol. 2012, 7 496-505.

Mishra et al., "Inhibiting Nucleation of Amyloid Structure in a Huntintin Fragment by Targeting Aplha-Helix Rich Oligomeric Intermediates," J. Mol Biol. Feb. 3, 2012; 415(5): 900-917.

Nagai et al., "Inhibition of Polyglutamine Protein Aggregation and Cell Death by Novel Peptides Identified by Phage Display Screening," The Journal of Biological Chemistry, vol. 275, No. 14, Apr. 7, 2000, 10437-10442.

Linford, et al., "Measurement of Lifespan in *Drosophila melanogaster*," JOVe Journal of Visualized Experiments, Jan. 2013, 71, e50068, 1-9.

Nalavade, et al., "Mechanisms of RNA-lnduced Toxicity in CAG Repeat Disorders," Cell Death and Disease (2013) 4, e752, 1-11.

Muqit et al., "Modeling Neurodegenerative Diseases in *Drosophila*: a Fruitful Approach," Nature Reviews, Neuroscience, vol. 3, Mar. 2002, 237-243.

Sanchez et al., "Pivotal Role of Oligomerization in Expanded Polyglutamine Neurodegenerative Disorders," Nature, vol. 421, Jan. 23, 2003, 373-379.

Takahashi, et al., "Polyglutamine Diseases: Where does Toxicity Come From? What is Toxicity? Where are we Going?," Journal of Molecular Cell Biology (2010), 2, 180-191.

Williams, et al., "Polyglutamine Neurodegeneration: Protein Misfolding Revisted," Trends Neurisci, Oct. 2008, 31(10): 521-528.

Raussens et al., "Protein Concentration is not an Absolute Prerequisite or the Determination of Secondary Structure from Circular Dichroism spectra: a New Scaling Method," Analytical Biochemistry, 319 (2003) 114-121.

Popiel et al., "Protein Transduction Domain-Mediated Delivery of QBP1 Suppresses Polyglutamine-lnduced Neurodegeneration In Vivo," Molecular Therapy, Vo. 15, No. 2, Feb. 2007, 303-309.

Fiszer, et al., "RNA Toxicity in Polyglutamine Disorders: Concepts, Models and Progress of Research," J Mol Med (2013) 91:683-691.

Li et al., "RNA Toxicity is a Component of Ataxin-3 Degeneration in *Drosophila*," Nature, vol. 453, Jun. 19, 2008, 1107-1112.

Li et al., "Selection of Peptides That Target the Aminoacyl-tRNA Site of Bacterial 16S Ribosomal RNA," Biochemistry, Sep. 8, 2009; 48(35): 8299-8311.

Wong et al., "Targeting Toxic RNA's that Cause Myotonic Dystrophy Type 1 (DM1) with a Bisamidinium Inhibitor," J. Am. Chem. Soc. 2014, 136, 6355-6361.

Orr et al., "Trinucleotide Repeat Disorders," Annu. Rev. Neurosci. 2007.30:575-621.

\* cited by examiner

```
                       SEQUENCE LISTING

<160> NUMBER OF SEQ ID NOS: 7

<210> SEQ ID NO 1
<211> LENGTH: 21
<212> TYPE: PRT
<213> ORGANISM: Artificial Sequence
<220> FEATURE:
<223> OTHER INFORMATION: synthetic peptide sequence - P3L

<400> SEQUENCE: 1

Ala Glu Ile Arg Leu Val Ser Lys Asp Gly Lys Ser Lys Gly Ile Ala
1               5                   10                  15

Tyr Ile Glu Phe Lys
            20

<210> SEQ ID NO 2
<211> LENGTH: 13
<212> TYPE: PRT
<213> ORGANISM: Artificial Sequence
<220> FEATURE:
<223> OTHER INFORMATION: synthetic peptide sequence - P3

<400> SEQUENCE: 2

Asp Gly Lys Ser Lys Gly Ile Ala Tyr Ile Glu Phe Lys
1               5                   10

<210> SEQ ID NO 3
<211> LENGTH: 77
<212> TYPE: PRT
<213> ORGANISM: Artificial Sequence
<220> FEATURE:
<223> OTHER INFORMATION: synthetic peptide sequence - RRM1

<400> SEQUENCE: 3

Phe Asn Leu Phe Ile Gly Asn Leu Asn Pro Asn Lys Ser Val Ala Glu
1               5                   10                  15

Leu Lys Val Ala Ile Ser Glu Pro Phe Ala Lys Asn Asp Leu Ala Val
            20                  25                  30

Val Asp Val Arg Thr Gly Thr Asn Arg Lys Phe Gly Tyr Val Asp Phe
        35                  40                  45

Glu Ser Ala Glu Asp Leu Glu Lys Ala Leu Glu Leu Thr Gly Leu Lys
    50                  55                  60

Val Phe Gly Asn Glu Ile Lys Leu Glu Lys Pro Lys Gly
65                  70                  75

<210> SEQ ID NO 4
<211> LENGTH: 74
<212> TYPE: PRT
<213> ORGANISM: Artificial Sequence
<220> FEATURE:
<223> OTHER INFORMATION: synthetic peptide sequence - RRM2

<400> SEQUENCE: 4

Arg Thr Leu Leu Ala Lys Asn Leu Ser Phe Asn Ile Thr Glu Asp Glu
1               5                   10                  15

Leu Lys Glu Val Phe Glu Asp Ala Leu Glu Ile Arg Leu Val Ser Gln
            20                  25                  30

Asp Gly Lys Ser Lys Gly Ile Ala Tyr Ile Glu Phe Lys Ser Glu Ala
        35                  40                  45
```

```
Asp Ala Glu Lys Asn Leu Glu Glu Lys Gln Gly Ala Glu Ile Asp Gly
        50                  55                  60

Arg Ser Val Ser Leu Tyr Tyr Thr Gly Glu
 65                  70

<210> SEQ ID NO 5
<211> LENGTH: 75
<212> TYPE: PRT
<213> ORGANISM: Artificial Sequence
<220> FEATURE:
<223> OTHER INFORMATION: synthetic peptide sequence - RRM3

<400> SEQUENCE: 5

Lys Thr Leu Val Leu Ser Asn Leu Ser Tyr Ser Ala Thr Glu Glu Thr
 1               5                  10                  15

Leu Gln Glu Val Phe Glu Lys Ala Thr Phe Ile Lys Val Pro Gln Asn
                20                  25                  30

Gln Gln Gly Lys Ser Lys Gly Tyr Ala Phe Ile Glu Phe Ala Ser Phe
            35                  40                  45

Glu Asp Ala Lys Glu Ala Leu Asn Ser Cys Asn Lys Met Glu Ile Glu
        50                  55                  60

Gly Arg Thr Ile Arg Leu Glu Leu Gln Gly Pro
 65                  70                  75

<210> SEQ ID NO 6
<211> LENGTH: 11
<212> TYPE: PRT
<213> ORGANISM: Artificial Sequence
<220> FEATURE:
<223> OTHER INFORMATION: synthetic peptide sequence - QBP1

<400> SEQUENCE: 6

Ser Asn Trp Lys Trp Trp Pro Gly Ile Phe Asp
 1               5                  10

<210> SEQ ID NO 7
<211> LENGTH: 23
<212> TYPE: PRT
<213> ORGANISM: Artificial Sequence
<220> FEATURE:
<223> OTHER INFORMATION: Synthetic construct

<400> SEQUENCE: 7

Ala Ala Ser Ser Gly Val Ser Thr Pro Gly Ser Ala Gly His Asp Ile
 1               5                  10                  15

Ile Thr Glu Gln Pro Arg Ser
                20
```

PEPTIDYLIC INHIBITORS OF NUCLEOLIN (NCL) TARGETING CAG-REPEAT RNA TOXICITY AND METHODS FOR REDUCING POLYQ-MEDIATED TOXICITY IN POLYQ DISEASES

REFERENCE TO A "SEQUENCE LISTING" SUBMITTED AS ASCII TEXT FILES VIA EFS-WEB

The Sequence Listing written in file 080015-018100US-0970537_SequenceListing.txt created on Jul. 28, 2017, 3,776 bytes, machine format IBM-PC, MS-Windows operating system, in accordance with 37 C.F.R. §§ 1.821—to 1.825, is hereby incorporated by reference in its entirety for all purposes.

BACKGROUND OF THE INVENTION

Many neurodegenerative diseases, including Alzheimer's and Parkinson's diseases, are caused by protein misfolding. Cellular proteins that adopt abnormal pathogenic conformations oligomerize and subsequently form soluble and/or insoluble aggregates in cells causing neuronal dysfunction and death. Polyglutamine (polyQ) diseases belong to the protein misfolding disease group. It is now known that polyQ toxicity is attributed to the toxic gain-of-function nature of misfolded disease proteins that harbour the expanded polyQ domain. Unfolded protein response (UPR) is one inducible cellular protective pathway that responds to the emergence of misfolded proteins in cells. It has been reported that this mechanism is involved in neurodegenerative diseases, including polyglutamine-induced neurodegeneration. UPR can be mediated by the interaction between misfolded proteins in the endoplasmic reticulum and the molecular chaperone GRP78/BiP, and this interaction would cause the activation of UPR sensors, including activating transcription factor 6 (ATF6), inositol requiring 1 (IRE1) and PKR-like endoplasmic reticulum kinase (PERK). The induction of GRP78/BiP expression has been used as a reliable indicator of UPR. Upregulation of GRP78/Bip has been observed in polyQ degeneration, which clearly indicates the involvement of protein misfolding in polyQ pathogenesis. It is likely, however, that there are other mechanisms involved in polyQ diseases. In particular, the mRNA transcripts that encode the polyQ peptides can play a role in these diseases, especially when the mRNAs encode the polyQ portion as an expanded CAG triplet nucleotide repeat. Such expanded CAG-RNAs are known to contribute to cytotoxicity through mechanisms that are independent of polyQ-mediated cytotoxicity.

Accordingly, there is a continued need to develop new and effective methods and compositions for treating polyQ diseases by reducing or eliminating cytotoxicty induced by the expanded CAG-RNA molecules. This invention fulfills this and other related needs.

BRIEF SUMMARY OF THE INVENTION

The present inventors surprisingly discovered that certain fragments of the nucleolin protein (NCL) can directly interact with CAG-repeat RNA and suppress CAG-repeat RNA toxicity. Thus, this invention provides novel methods and compositions useful for treating a polyQ disease.

In the first aspect, the present invention provides an isolated polypeptide comprising (1) a core sequence, which is a fragment of the NCL protein comprising SEQ ID NO:1; and (2) a heterologous amino acid sequence, provided that the polypeptide does not comprise the full length NCL protein. In some embodiments, the heterologous amino acid sequence is a TAT peptide. In some embodiments, the core amino acid sequence is SEQ ID NO:1. In some embodiments, the polypeptide consists of SEQ ID NO:1 and a TAT peptide, with the TAT peptide located at the N-terminus of the polypeptide and SEQ ID NO:1 located at the C-terminus of the polypeptide.

In a related aspect, the present invention provides a composition comprising the polypeptide described above and herein along with a physiologically acceptable excipient. In some embodiments, the polypeptide consists of SEQ ID NO:1 and a TAT peptide, which is at the N-terminus of the polypeptide. In some embodiments, the polypeptide further comprises another therapeutic agent effective for treating a polyQ disease, e.g., a polyQ protein toxicity inhibitor such as P42 or QBP1.

In a second aspect, the present invention provides a method for treating a polyQ disease in a subject. The method involves a step of administering to the subject an effective amount of a polypeptide comprising an NCL RRM domain. This polypeptide encompasses a fragment of NCL comprising SEQ ID NO:1 but does not encompass the full length NCL. This polypeptide optionally further comprises one or more heterologous amino acid sequences, which may be located at the N-terminus and/or C-terminus of the polypeptide. Even with the addition of the heterologous amino acid sequence(s), this polypeptide does not include a full length NCL sequence.

In some embodiments, the polypeptide consists of SEQ ID NO:1 and a TAT peptide, which is at the N-terminus of the polypeptide. In some embodiments, another therapeutic agent effective for treating a polyQ disease is co-administered to the patient. Such agent may be a polyQ protein toxicity inhibitor, such as P42 or QBP1. In some embodiments, the polypeptide is administered orally or by injection intravenously, intramuscularly, or subcutaneously, intraperitoneally. In some embodiments, the polypeptide is administered once daily, weekly, or monthly. Frequently, about 1-10,000 mg, about 10-1,000 mg, about 10-100 mg, about 20-50 mg, or about 10, 20, 30, 40, or 50 mg of the polypeptide is administered each time to the subject per kg of the subject's body weight. In practicing the method, the subject often has been diagnosed with a polyQ disease or is at risk of developing a polyQ disease.

In a related aspect, the present invention indicates the use of a polypeptide comprising an NCL RRM domain in the manufacture of a medicament for treating a polyQ disease in a subject. As described herein, this polypeptide encompasses a fragment of NCL comprising SEQ ID NO:1 but does not encompass the full length NCL. This polypeptide optionally may further comprise one or more heterologous amino acid sequences, which can be located at the N-terminus and/or C-terminus of the polypeptide. Even with the addition of the heterologous amino acid sequence(s), this polypeptide does not include a full length NCL sequence. Typically, the medicament comprises a physiologically acceptable excipient. In some embodiments, the polypeptide consists of SEQ ID NO:1 and a TAT peptide, with the TAT peptide located at the N-terminus of the polypeptide and SEQ ID NO:1 located at the C-terminus of the polypeptide. In some embodiments, the medicament is formulated for injection, such as for intravenous, intramuscular, intraperitoneal, or subcutaneous injection. Or the medicament may be formulated for oral administration. In some embodiments, the medicament further comprises another therapeutic agent effective for treating a polyQ disease (e.g., a polyQ protein toxicity inhibitor such as P42 or QBP1). Quite often, the medicament is formulated in a dose form containing an effective amount of the polypeptide for each administration.

In a third aspect, the present invention provides a kit for treating a polyQ disease. The kit comprises a container containing a pharmaceutical composition comprising a polypeptide described herein, which is capable of inhibiting expanded CAG-RNA mediated toxicity as verified in an in vitro or in vivo assay. In some embodiments, the kit further comprises a second container containing a second therapeutic agent effective for treating a polyQ disease, such as polyQ protein toxicity inhibitor P42 or QBP1. In some embodiments, the kit further comprises informational material providing instructions on administration of the pharmaceutical composition.

DEFINITIONS

Figure 1:
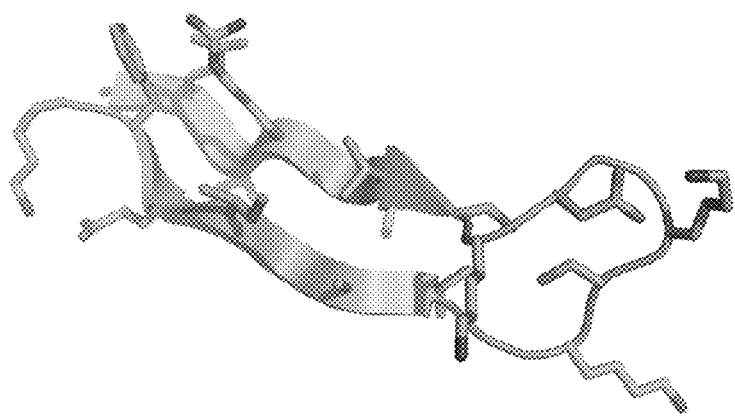
FIG. 1: Predicted P3L Structure.

The term "inhibiting" or "inhibition," as used herein, refers to any detectable negative effect on a target biological process, such as expanded CAG-RNA mediated or PolyQ-mediated toxicity. Typically, an inhibition of expanded CAG-RNA mediated or PolyQ-mediated toxicity is reflected in a decrease of at least 10%, 20%, 30%, 40%, 50%, 60%, 70%, 80%, 90% or higher, including 100% or complete elimination, of one or more hallmarks of expanded CAG-RNA mediated or PolyQ-mediated toxicity as described herein, when compared to a control not given the "inhibition" treatment, such as treatment by administration of small molecule therapeutics described herein. On the other hand, inhibition of expanded CAG-RNA mediated or PolyQ-mediated toxicity may also be manifested as increased cell survival, demonstrated in an increase of at least 50%, 60%, 70%, 80%, 90%, 100%, 200%, 300%, 500% or more in the number or length of time of cell survival in the pertinent tissues within the recipient body after the small molecule administration in comparison to a control that has not received the same treatment.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a core amino acid sequence responsible for expanded CAG-RNA binding has at least 80% identity, preferably 85%, 90%, 91%, 92%, 93, 94%, 95%, 96%, 97%, 98%, 99%, or 100% identity, to a reference sequence, e.g., SEQ ID NO:1 or 2), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to an inhibition or reduction in the likelihood or severity of such occurrence or a delay in such occurrence.

A "polyQ disease," as used herein, refers to a disease or condition that is associated with, caused by, or exacerbated by, RNA containing an expanded long repeats of CAG trinucleotides (expanded CAG-RNA) and/or polyQ polypeptides, which may be encoded by the expanded CAG-RNA. PolyQ diseases include those diseases, conditions, and symptoms that result from nucleolar stress or endoplasmic reticulum stress caused by expanded CAG-RNA, polyQ polypeptides, or both. As such, the presence of a polyQ disease can be observed at a cellular level by detecting or measuring one or more of the hallmarks of expanded CAG-RNA mediated cytotoxicity or polyQ-mediated cytotoxicity. Additionally, the presence of a polyQ disease can be indicated by the presence of expanded CAG-RNA or polyQ polypeptides in pertinent cells/tissues of a person being tested for the disease. Furthermore, cells or tissues taken from or present in the body of a patient suffering from polyQ disease or suspected to suffer from a polyQ disease, e.g., due to hereditary patterns, can exhibit one or more of the hallmarks of expanded CAG-RNA mediated cytotoxicity or polyQ-mediated cytotoxicity to indicate the presence of a polyQ disease, regardless of whether clinical symptoms of the polyQ disease are apparent at the time. Exemplary polyQ diseases include Huntington's Disease (HD), Dentatorubropallidoluysian atrophy (DRPLA), Spinocerebellar ataxia (SCA) Type 1, Spinocerebellar ataxia Type 2, Machado-Joseph Disease (MJD/SCA3), Spinocerebellar ataxia Type 6, Spinocerebellar ataxia Type 7, Spinocerebellar ataxia Type 17, and Spinal and bulbar muscular atrophy, X-linked 1 (SMAX1/SBMA).

The term "effective amount," as used herein, refers to an amount that produces therapeutic effects for which a substance is administered. The effects include the prevention, correction, or inhibition of progression of the symptoms of a disease/condition and related complications to any detectable extent, e.g., one or more of the hallmarks of expanded CAG-RNA mediated cytotoxicity or polyQ-mediated cytotoxicity. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range of ±10% of the value.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

"Translocation sequence" or "transduction sequence" refers to a peptide or protein (or active fragment or domain thereof) sequence that directs the movement of a protein from one cellular compartment to another, or from the extracellular space through the cell or plasma membrane into the cell. Examples include the TAT transduction domain (see, e.g., S. Schwarze et al., Science 285 (Sep. 3, 1999); penetratins or penetratin peptides (D. Derossi et al., Trends in Cell Biol. 8, 84-87); and Herpes simplex virus type 1 VP22 (A. Phelan et al., Nature Biotech. 16, 440-443 (1998). Translocation peptides can be fused (e.g. at the amino and/or carboxy terminus), conjugated, or coupled to a polypeptide of the present invention, in order to produce a conjugate compound such as a fusion peptide that may pass into target cells, or through the blood brain barrier and into target cells more easily.

As used herein, the term "nucleolin" or "NCL" refers to the nucleolin protein. Exemplary nucleolin proteins include those of the Chinese Hamster (Genbank Accession No. AAA36966.1), the golden hamster (Genbank Accession No. P08199.2), the Norwegian Rat (Genbank Accession No. EDL75577.1), the house mouse (Genbank Accession No. EDL40222.1), and human nucleolin (Genbank Accession No. EAW70962.1). In some embodiments of this invention, peptides derived from NCL are provided for treatment of expanded CAG-RNA mediated cytotoxicity or polyQ disease. In any case, such peptides are less than full length NCL. For example, such peptides can be shorter in length, e.g., less than 714 amino acids in length or less than about 30, 50, 75, 100, 150, 200, 250, 300, 350, 400, 500, 600, or 700 amino acids in length.

As used herein, a "polypeptide comprising an NCL RNA recognition motif (RRM) domain" refers to a polypeptide containing a core amino acid sequence that generally corresponds to the amino acid sequence of an RNA recognition motif of nucleolin (NCL). Nucleolin contains three RRM domains, including:

```
RRM1, SEQ ID NO: 3:
FNLFIGNLNPNKSVAELKVAISEPFAKNDLAVVDVRTGTNRKFGY
VDFESAEDLEKALELTGLKVFGNEIKLEKPKG;
```

```
RRM2, SEQ ID NO: 4:
RTLLAKNLSFNITEDELKEVFEDALEIRDGKSKGILVSQAYIE
FKSEADAEKNLEEKQGAEIDGRSVSLYYTGE;
and
```

```
RRM3, SEQ ID NO: 5:
KTLVLSNLSYSATEETLQEVFEKATFIKVPQNQQGKSKGY
AFIEFASFEDAKEALNSCNKMEIEGRTIRLELQGP
```

These core amino acid sequences may contain some variations such as amino acid deletion, addition, or substitution, but should maintain a substantial level sequence homology (e.g., at least 80%, 85%, 90%, 95%, 98%, or higher sequence homology) to SEQ ID NO:3, SEQ ID NO:4, or SEQ ID NO:5.

Moreover, RRM2 domains, and homologs thereof, are capable of binding RNA containing 1, 2, 3, 4, 5, 10, 15, 20, 25, 30, 35, 40, 50, 60, 75, or more CAG triplet nucleotide repeats. In addition to this core sequence that is responsible for the polypeptide's ability to bind to expanded CAG-RNA, one or more amino acid sequences of a homologous origin (e.g., additional sequence derived from the same protein, NCL) or a heterologous origin (e.g., an amino acid sequence derived from another unrelated protein) can be included in the polypeptide at the N- and/or C-terminus.

Some examples of the "polypeptide comprising an NCL RRM domain" include SEQ ID NOs:1-5. However, as used herein, a "polypeptide comprising an NCL RRM domain" does not comprise the full length wild-type NCL. For example, in some cases, the "polypeptide comprising an NCL RRM domain" can be shorter than a full length NCL RRM domain, e.g., less than about 25, 30, 40, 50, 60, 70, 80, 90, or 100 amino acids in length. Optionally, one or more peptides of a heterologous origin, for example, an affinity or epitope tag (such as a GST tag), can be included in the polypeptide at either or both ends to facilitate purification, isolation, or immobilization of the polypeptide. If a heterologous amino acid sequence is included at both ends, each end can be fused to the same heterologous amino acid sequence, or each end can be fused to a different sequence. One example of a polypeptide comprising an NCL RRM domain is a fusion peptide of TAT and SEQ ID NO:1 or 2.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

As used herein, the terms "(CAG)$_n$-mediated toxicity," "expanded CAG-RNA mediated cytotoxicity," and the like refer to cytotoxicity caused by expanded CAG-RNA. Expanded CAG-RNA mediated toxicity can result in nucleolar stress and cell death. Expanded CAG-RNA mediated toxicity can be inferred by detecting or measuring one or more of (i) rRNA upstream control element hypermethylation, (ii) a decrease in rRNA transcription, (iii) a decrease in binding of NCL to the rRNA locus, (iv) an increase in binding between ribosomal proteins and MDM2, (v) stabilization of p53, (vi) accumulation of p53 in the mitochondria, (vii) release of Bcl-xL from Bak, (viii) release of cytochrome c from the mitochondria, (ix) caspase activation, and (x) apoptosis or cell death.

As used herein, the terms "PolyQ-mediated cytotoxicity," "PolyQ-mediated toxicity," and the like refer to cytotoxicity caused by polypeptides that contain polyglutamine amino acid sequences. PolyQ-mediated cytotoxicity can result in cellular stress, endoplasmic reticulum stress, an unfolded protein response, and cell death. PolyQ-mediated cytoxicity can be inferred by detecting or measuring one or more of (i) GRP78/BiP upregulation, (ii) caspase activation, and (iii) apoptosis or cell death. PolyQ-mediated cytotoxicity can be observed independently of expanded CAG-RNA mediated cytotoxicity by measuring GRP78/BiP upregulation as explained herein. Similarly, expanded CAG-RNA mediated cytotoxicity can be observed independently of polyQ-mediated cytotoxicity by measuring one or more of rRNA hypermethylation, NCL binding to rRNA locus, the level of rRNA expression, and binding between ribosomal proteins and MDM2 as explained herein.

RNA that contains CAG triplet nucleotide repeats can cause expanded CAG-RNA mediated cytotoxicity and polyQ-mediated cytotoxicity when the CAG repeats are translated. In some cases, the CAG repeats are not in a translated region and the expanded CAG-RNA can cause expanded CAG-RNA mediated cytotoxicity but not polyQ-mediated cytotoxicity. Similarly, if a polyglutamine polypeptide is encoded by an mRNA that does not contain CAG triplet nucleotide repeats, it can cause polyQ-mediated cytotoxicity but not expanded CAG-RNA mediated cytotoxicity. For example, a polyglutamine polypeptide can be encoded by CAG/A repeats (alternating CAG and CAA, which both encode glutamine), CAA/G repeats (alternating CAA and CAG), CAA repeats, or a combination thereof. Cells that contain expanded CAG-RNA or polyQ polypeptides can be detected by detecting expanded CAG-RNA or polyQ peptide directly, or by detecting or measuring any of the hallmarks of expanded CAG-RNA toxicity or polyQ peptide toxicity.

The term "consisting essentially of," when used in the context of describing a composition containing an active ingredient, refer to the fact that the composition does not contain other ingredients possessing any similar or relevant biological activity. For example, a composition consisting essentially of an inhibitor of expanded CAG-RNA mediated or PolyQ-mediated toxicity is a compound that does not contain other modulators such as enhancers or inhibitors of expanded CAG-RNA mediated or PolyQ-mediated toxicity.

DETAILED DESCRIPTION OF THE INVENTION

I. Introduction

Polyglutamine (polyQ) diseases are a group of late-onset, dominant genetic disorders characterized by expanded CAG repeats in the coding region of the associated genes, which are translated into expanded polyQ domains in disease proteins. Traditionally, the toxicity of polyQ disease was considered to be only caused by the expanded polyQ proteins. However, accumulating evidence demonstrate that the expanded CAG-repeat RNA is also a toxic component of polyQ pathogenesis. Recently, it was demonstrated that the expanded CAG-repeat RNA triggers nucleolar stress to induce apoptosis.

Figure 4:
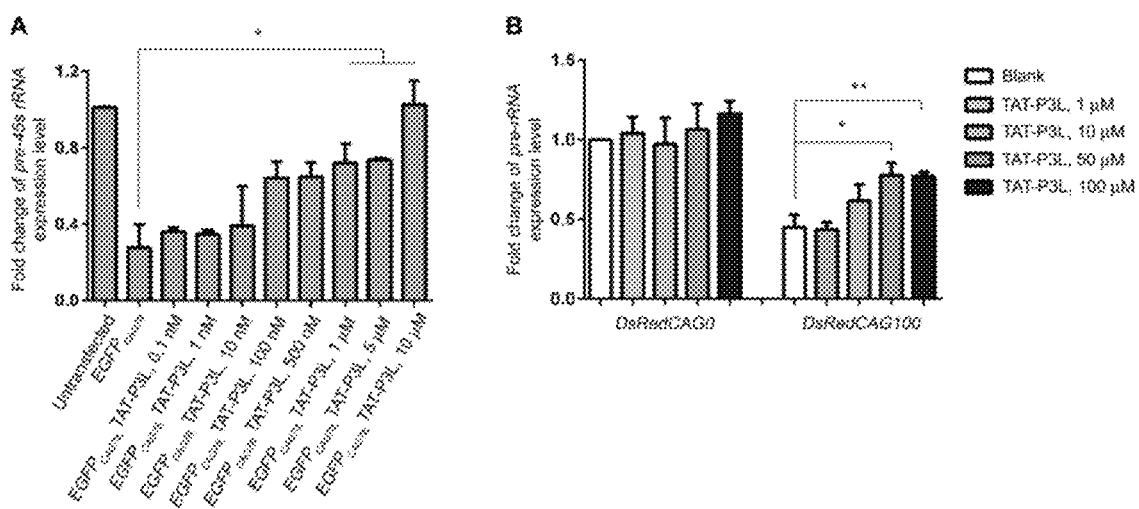
FIG. 4: P3L concentration-dependently restored pre-45s rRNA and pre-rRNA expression level in polyQ disease in vitro and in vivo. (A) TAT-P3L restored the expression level of pre-45s rRNA in $EGFP_{CAG78}$ RNA expressing-HEK293 cells in a concentration-dependent manner. (B) TAT-P3L restored the expression level of pre-rRNA in $DsRed_{CAG100}$ (RNA toxicity only) flies in a concentration-dependent manner.

Recently, the inventors' research group demonstrated that the expanded CAG-repeat RNA could directly bind to nucleolin (NCL), a nucleolar protein that regulates rRNA transcription. The direct interaction of expanded CAG-repeat RNA and NCL reduces rRNA levels and ribosome formation, and further leads to accumulation of unassembled ribosomal proteins. These ribosomal proteins bind to the E3 ubiquitin ligase MDM2 and trigger a chain of events ultimately leading to mitochondrial accumulation of p53 and apoptosis. This represents the nucleolar stress pathway of the expanded CAG-repeat RNA toxicity. Based on their discovery of NCL interaction with CAG-repeated RNA, the present inventors have previously developed a polypeptide or polynucleotide-based therapeutic strategy for treating polyQ diseases, see, e.g., U.S. Patent Application Publication No. 2014/0357578. An 8-amino acid fragment of the NCL RRM2 domain termed P3 (SEQ ID NO:2) is reported to be an effective inhibitor of NCL interaction with CAG-repeated RNA and therefore an effective therapeutic agent for treating polyQ diseases. The present inventors have now unexpectedly discovered a slightly longer fragment of the NCL RRM2 domain, termed P3L (SEQ ID NO:1), is far more effective than P3 as an inhibitor of NCL interaction with CAG-repeated RNA. Specifically, P3L is believed to adopt a 3D conformation different from P3 and is capable of rescuing polyQ neurodegeneration in vivo and in vitro. Compared to P3, P3L interacts directly with the CAG-repeat RNA with a much higher affinity, in some cases an about 10-fold higher affinity is observed. P3L also exhibits over 5-times higher activity compared to P3 in suppressing expanded CAG-repeat RNA toxicity both in vivo and in vitro (see FIG. 9). It has been further discovered that P3L relieves the expanded CAG-repeat RNA-induced nucleolar stress in a dose-dependent manner (see FIG. 4). In addition, P3L has relatively low cellular toxicity, with no observed cytotoxicity at a concentration up to 25 µM (see FIG. 8B). P3L and its fusion peptides (comprising at least one heterologous amino acid sequence) are therefore considered useful therapeutic agents for treating polyQ diseases.

II. Compositions

A. Inhibitors of $(CAG)_n$-Mediated Toxicity

In some embodiments, compositions are provided that reduce $(CAG)_n$-mediated toxicity in a cell. Reduction of $(CAG)_n$-mediated toxicity can, in some cases, restore rRNA transcription in expanded CAG RNA-expressing cells. For example, synthetic peptides are provided that can bind to or sequester toxic RNA species. In some cases, the synthetic peptides are fragments derived from full-length nucleolin (NCL) but do not encompass the full-length NCL. For example, the synthetic peptides may be derived from an RNA recognition motif (RRM) of full-length nucleolin. In some cases, the synthetic peptides are derived from the RRM2 domain of NCL. The peptides optionally may include one or more additional amino acid sequences from a heterologous origin, i.e., a source other than the NCL protein.

In some cases, compositions for treating $(CAG)_n$-mediated RNA toxicity in a cell include one or more of the above synthetic peptides. For example, compositions for treating $(CAG)_n$-mediated RNA toxicity in a cell can include peptide P3 and/or P3L as well as those described in U.S. Patent Application Publication No. 2014/0357578.

In some cases, the peptides are conservatively substituted at one or more of 1, 2, 3, 4, 5, 6, 7, 8, 9, 10, 11, 12, 13, and 14 positions. The peptides can also be substituted with non-natural amino acids, such as D-amino acids or chemically modified natural amino acids. In some cases, the peptides are truncated. Truncated peptides include peptides in which one or more amino or carboxy terminal residues are removed. In some cases, the peptides are internally deleted such that one or more amino acids that are not at the amino or carboxy terminus are removed. In some cases, the peptides can be modified by the addition of one or more amino acids at the amino or carboxy terminus. For example, a linker or purification tag can be fused to the amino or carboxy terminus. Alternatively, the peptides can be inserted into a scaffold region of a protein, polypeptide, or other molecule as described herein. A scaffold may provide enhanced stability of the peptide in the cell, and may improve binding by reducing the conformational freedom of the peptide or influencing its three-dimensional structure.

For example, one or more of the peptides can be inserted into the CDR region of an antibody scaffold. Alternatively, non-immunoglobulin protein scaffolds can be used as peptide frameworks. See, e.g., Ku et al. (*Proc. Natl. Acad. Sci. U.S.A.* 92 (14):6552-6556 (1995)) disclosing the use of cytochrome b562 as a scaffold; U.S. Pat. Nos. 6,818,418 and 7,115,396 disclosing the use of a fibronectin or fibronectin-like protein scaffolds; Beste et al. (*Proc. Natl. Acad. Sci. U.S.A.* 96 (5):1898-1903 (1999)) disclosing a lipocalin-based scaffold; U.S. Pat. No. 5,770,380 disclosing a synthetic rigid, non-peptide organic scaffold of calixarene, attached with one or more multiple variable peptide loops used as binding sites; and Murali et al. (*Cell Mol Biol* 49 (2):209-216 (2003)) describing a methodology for reducing antibodies into smaller peptidomimetics, termed "antibody like binding peptidomimetics" (ABiP) which may also be useful as a protein scaffold.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody scaffolds can also include such compounds.

B. Production of Peptides that Inhibit $(CAG)_n$-Mediated RNA Toxicity i. General Recombinant Technology Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a nucleolin gene, a polynucleotide encoding a polypeptide comprising the expanded CAG-RNA binding domain RRM2 or a peptide derived therefrom, and synthetic oligonucleotides can be verified after cloning or subcloning using, e.g., the chain termination method for sequencing double-stranded templates of Wallace et al., *Gene* 16: 21-26 (1981).

ii. Coding Sequence for a Polypeptide Comprising an NCL RRM Domain

Polynucleotide sequences encoding nucleolin or its RRM domains have been determined and may be obtained from a commercial supplier or recombinantly produced.

Upon acquiring a nucleic acid sequence encoding a an RNA-recognition motif or encoding a peptide that binds expanded CAG-RNA, the coding sequence can be further modified by a number of well-known techniques such as restriction endonuclease digestion, PCR, and PCR-related methods to generate coding sequences for RRM2-related polypeptides, including RRM mutants and polypeptides comprising an expanded CAG-RNA binding sequence derived from nucleolin. The polynucleotide sequence encoding a desired RRM-related polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding an RRM-related polypeptide. See, e.g., Zhang et al., *Proc. Natl. Acad. Sci. USA*, 94: 4504-4509 (1997); and Stemmer, Nature, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

iii. Modification of Nucleic Acids for Preferred Codon Usage in a Host Organism

The polynucleotide sequence encoding a polypeptide comprising an NCL RRM can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the RRM-comprising polypeptides.

iv. Chemical Synthesis of a Polypeptide Comprising an NCL RRM Domain

A polypeptide comprising an expanded CAG-RNA binding sequence, e.g., an NCL RRM domain, can also be chemically synthesized using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis*, in *The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

B. Expression and Purification of Peptides that Inhibit $(CAG)_n$-Mediated RNA Toxicity Following verification of the coding sequence, a polypeptide comprising an NCL RRM domain of the present invention can be produced using routine techniques in the field of recombinant genetics, relying on the polynucleotide sequences encoding the polypeptide disclosed herein.

i. Expression Systems

To obtain high level expression of a nucleic acid encoding a polypeptide comprising an NCL RRM domain of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the polypeptide comprising an NCL RRM domain in host cells. A typical expression cassette thus contains a promoter operably linked to the nucleic acid sequence encoding the polypeptide comprising an NCL RRM domain and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the RRM-related polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an RRM-related polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

ii. Transfection Methods

Standard transfection methods are used to produce bacterial, mammalian, yeast, insect, or plant cell lines that express large quantities of a polypeptide comprising an NCL RRM domain, which is then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the RRM-related polypeptide.

iii. Purification of Recombinantly Produced Polypeptides

Once the expression of a recombinant polypeptide comprising an NCL RRM domain in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the polypeptides comprising an NCL RRM domain of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a polypeptide comprising an NCL RRM domain, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., a polypeptide comprising an NCL RRM domain, is expressed in host cells in a soluble form, its purification can follow the standard protein purification procedure described below. This standard purification procedure is also suitable for purifying a polypeptide comprising an NCL RRM domain obtained from chemical synthesis.

(a) Solubility Fractionation

Often as an initial step, and if the protein mixture is complex, an initial salt fractionation can separate many of the unwanted host cell proteins (or proteins derived from the cell culture media) from the recombinant protein of interest, e.g., a polypeptide comprising an NCL RRM domain of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

(b) Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a polypeptide comprising an NCL RRM domain. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

(c) Column Chromatography

The proteins of interest (such as a polypeptide comprising an NCL RRM domain of the present invention) can also be separated from other proteins on the basis of their size, net surface charge, hydrophobicity, or affinity for ligands. In addition, antibodies raised against a segment of nucleolin such as an RNA recognition motif can be conjugated to column matrices and the RRM-related polypeptide immunopurified. All of these methods are well known in the art.

It will be apparent to one of skill that chromatographic techniques can be performed at any scale and using equipment from many different manufacturers (e.g., Pharmacia Biotech).

iv. Verification of Activity

Once a polypeptide comprising an NCL RRM domain is chemically synthesized or recombinantly produced, such as one generally fitting the structural profile described herein, the polypeptide can be then tested to verify its ability to suppress or inhibit cytotoxicity induced by CAG-repeat RNA in an in vitro or in vivo assay, e.g., any one of those known in the pertinent research field or described herein. An effective polypeptide can then be used in a therapeutic scheme for treating a patient suffering from or at risk of developing a polyQ disease, such as a human patient who has been diagnosed with a polyQ disease or who has a family history of a polyQ disease. Use of an effective polypeptide also encompasses the use of the polypeptide for manufacturing a medicament or a kit that is to be used for treating a polyQ disease.

C. Inhibitors of Polyglutamine (polyQ)-Mediated Toxicity

The present invention also provides inhibitors of polyQ mediated cytotoxicity. Such inhibitors include the peptide QBP1 (S N W K W W P G I F D, SEQ ID NO:6) or its homologs (at least 80%, 85%, 90%, 95%, or higher sequence homology) that are capable of binding polyglutamine. This core amino acid sequence may contain some variations such as amino acid deletion, addition, or substitution, but should maintain an affinity to polyglutamine. As described above, such a peptide may also be incorporated into a scaffold such as an antibody scaffold, a lipocalin scaffold, a calixarene scaffold, etc.

III. Methods

A. Identification of Compounds that Inhibit $(CAG)_n$-Mediated RNA Toxicity

An in vitro assay can be used to detect binding between nucleolin and expanded CAG-RNA or detect the binding between a polypeptide comprising an NCL RRM domain and expanded CAG-RNA and to identify compounds that are capable of inhibiting nucleolin:expanded CAG-RNA binding. Such an assay can be performed in the presence of nucleolin or a peptide derived therefrom, such as any one of P3 or P3L, and an expanded CAG-RNA, under conditions permitting binding. For convenience, one of the binding partners may be immobilized onto a solid support and/or labeled with a detectable moiety. A third molecule, such as an antibody (which may include a detectable label) to one of the binding partners, can also be used to facilitate detection.

In one embodiment, the expanded CAG-RNA can be labeled with a fluorophore and its intrinsic fluorescence anisotropy due to tumbling in solution can be measured. If a fluorescent molecule is excited with polarized light then the emission will also be polarized. The extent of polarization of the emission is usually described in terms of anisotropy (r). As molecules are tumbling in solution, the emitted light is then depolarized. The depolarization of the fluorescent molecule is dependent on the size and shape of the rotating molecule and also the viscosity of the solution. The smaller the molecule, the more rapidly it rotates and the more the light is depolarized and hence the lower the anisotropy. If a larger molecule interacts with the fluorescent molecule the rotation of the complex will be slower than of the unbound molecules and result in an increase in the fluorescence anisotropy. Inhibitors can be identified by incubating the complex in the presence of a test compound and measuring a reduction in fluorescence anisotropy as compared to a control in which the test compound is not added to the complex.

In some cases, the binding assays can be performed in a cell-free environment; whereas in other cases, the binding assays can be performed in a cell, frequently using cells recombinantly or endogenously expressing an appropriate expanded CAG-RNA molecule. For example, cells expressing an expanded CAG-RNA molecule can be contacted with a test compound and one or more markers of nucleolar stress can be assayed. Such markers include rRNA transcription, rRNA UCE hypermethylation, p53 stability, and apoptosis (e.g., as shown by a decrease in rhabdomeres per ommatidium in the eye of a fruit fly).

To screen for compounds capable of inhibiting nucleolin:expanded CAG-RNA binding, the above-described assays can be performed both in the presence and absence of a test compound, and the level of nucleolin:expanded CAG-RNA binding compared. If nucleolin:expanded CAG-RNA binding is suppressed in the presence of the test compound, for example, at a level of at least 10%, more preferably at least 20%, 30%, 40%, or 50%, or even higher, the test compound is then deemed an inhibitor nucleolin:expanded CAG-RNA binding and may be subject to further testing to confirm its ability to inhibit nucleolar stress.

In some cases, an inhibitor could be identified by detecting an increase in rRNA transcription relative to a control cell expressing an expanded CAG-RNA molecule that is not contacted with the test compound. As another example, an inhibitor could be identified by detecting a decrease in methylation of the rRNA UCE relative to a control cell expressing an expanded CAG-RNA molecule that is not contacted with the test compound. As yet another example, an inhibitor could be identified by detecting a decrease in p53 stabilization (e.g., a reduction in p53 accumulation) relative to a control cell expressing an expanded CAG-RNA molecule that is not contacted with the test compound. As yet another example, an inhibitor could be identified by detecting an increase in the number of rhabdomeres per ommatidium in the eye of a fruit fly relative to a control eye in which the cells express an expanded CAG-RNA molecule that is not contacted with the test compound. More details and some examples of such binding assays can be found in the Examples section of this application.

A binding assay is also useful for confirming that a polypeptide comprising an expanded CAG-RNA binding sequence can indeed specifically bind expanded CAG-RNA. For instance, a polypeptide comprising an RRM2 fragment (e.g., P3 or P3L) but not the full length NCL sequence can be recombinantly expressed, purified, and placed in a binding assay with expanded CAG-RNA, or expanded CAA/G-RNA, in which every alternate guanine nucleotide is substituted with adenine as a negative control. If deemed to have sufficient expanded CAG-RNA binding ability and specificity, the polypeptide sequence can then be used as a positive control for identifying inhibitors of NCL:expanded CAG-RNA binding. Similarly, a polypeptide comprising a core sequence with a high level of homology (e.g., 90%, 95% or higher) to any one of RRM2 fragment can be tested and, if appropriate, can be used as a positive control for identifying inhibitors of NCL:expanded CAG-RNA binding.

Inhibitors of NCL:expanded CAG-RNA binding can have diverse chemical and structural features. For instance, an inhibitor can be a non-functional NCL mutant that retains expanded CAG-RNA binding ability, an antibody that interferes with NCL:expanded CAG-RNA binding, or any small molecule or macromolecule that simply hinders the interaction between NCL and expanded CAG-RNA. Essentially any chemical compound can be tested as a potential inhibitor of NCL:expanded CAG-RNA binding. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. Identification of Compounds that Inhibit Polyglutamine-Mediated Toxicity

The triplet nucleotide CAG encodes for glutamine. Therefore, in general, diseases which exhibit expanded CAG-RNA mediated cytotoxicity also exhibit polyglutamine (polyQ)-mediated cytotoxicity. However polyQ-mediated cytotoxicity can be differentiated from expanded CAG-RNA mediated cytotoxicity in an appropriate assay.

For example, a cell can be transfected with an expression construct encoding for an expanded CAG-RNA that is not translated. In some cases, the CAG-RNA portion is not translated, while other portions of the expression construct are translated. For example, the present invention provides a DsRed$_{CAGn}$ expression cassette in which n can from about 20 to about 100, including 20, 30, 40, 50, 60, 70, 78, 80, 90, or 100. In the DsRed$_{CAGn}$ expression cassette, the expanded CAG-RNA is present in the 3' UTR of the mRNA encoded by the expression cassette. Thus, in a cell transfected with the expression cassette, the DsRed protein is translated and fluorescence can be detected to indicate successful transformation of the cell, but only CAG-RNA mediated cytotoxicity is exhibited. In this model, the length of the CAG expansion will generally correlate with increased CAG-RNA mediated cytotoxicity. For example, DsRed$_{CAG0}$ exhibits no discernible CAG-RNA mediated cytotoxicity, while DsRed$_{CAG100}$ exhibits a high level of CAG-RNA mediated cytotoxicity.

Conversely, a cell can be transfected with an expression cassette that encodes for a protein containing a polyQ sequence. If the cassette encodes the polyQ sequence by encoding an expanded CAG-RNA, then the cell will exhibit both CAG-RNA mediated cytotoxicity and polyQ cytotoxicity. However, if the construct encodes the polyQ sequence using CAA, CAG/A, or CAA/G (alternating CAA and CAG), then a transfected cell will exhibit polyQ cytotoxicity but not CAG-RNA mediated cytotoxicity. Such a cell can be identified because it will not exhibit hypermethylation of the UCE of the rRNA gene, or will not exhibit a reduction in rRNA transcription. However, the cell can exhibit markers of polyQ-mediated stress such as an increase in expression of a marker associated with polyQ-mediated stress.

GRP78/BiP is a marker that is specific for polyQ-mediated cytotoxicity as demonstrated by its upregulation in cells transfected with an expression construct encoding the MJD$_{CAA/G78}$ peptide and its lack of upregulation in cells transfected with the DsRed$_{CAG78}$ construct in which the CAG$_{78}$ triplet nucleotide repeat is in the 3' UTR. Similarly, polyQ peptide aggregation is specific for polyQ-mediated cytotoxicity. In contrast, rRNA transcription and hypermethylation of the UCE of the rRNA gene are markers that are specific for expanded CAG-RNA mediated cytotoxicity because rRNA transcription is reduced and hypermethylation is exhibited in cells transfected with the DsRed$_{CAG78}$ construct in which the CAG$_{78}$ triplet nucleotide repeat is in the 3' UTR but not in cells transfected with an expression construct encoding the MJD$_{CAA/G78}$ peptide. Therefore, expanded CAG-RNA and polyQ protein cytotoxicity can be independently monitored by measuring expression levels of rRNA and GRP78/BiP respectively in cells. In some cases, expanded CAG-RNA mediated cytotoxicity can be specifically monitored by detecting hypermethylation of the UCE of the rRNA gene or rRNA transcription and polyQ-mediated cytotoxicity can be specifically monitored by measuring expression of GRP78/BiP or aggregation of the polyQ peptide.

In one embodiment, a cell is transfected with a construct that causes polyQ mediated cytotoxicity but not expanded CAG-RNA mediated cytotoxicity, and contacted with a test compound. The cell can then be assayed for a reduction in polyQ mediated cytotoxicity. In another embodiment, a cell is transfected with a construct that causes polyQ mediated cytotoxicity and expanded CAG-RNA mediated cytotoxicity and contacted with a test compound. The cell can then be assayed for a reduction in polyQ mediated cytotoxicity, expanded CAG-RNA mediated cytotoxicity, or both. In this manner compounds that reduce expanded CAG-RNA mediated cytotoxicity, reduce polyQ-mediated cytotoxicity, or reduce both can be identified. Test compounds include peptide and small molecule chemical libraries as described above. Test compounds also include the QBP1 peptide, SEQ ID NO:6, or a derivative thereof. The QBP1 peptide or a derivative thereof can also be used as a positive control.

C. Methods of Treatment of PolyQ Disease

Provided herein are methods for treating polyQ disease in a cell that contains an RNA containing a (CAG)$_n$ triplet nucleotide repeat. Such methods include contacting the cell with an effective amount of a composition that reduces expanded-CAG RNA-mediated cytotoxicity. Methods of contacting can be performed in vitro and in vivo. In some cases, the RNA containing the (CAG)$_n$ triplet nucleotide repeat contains at least 10, 20, 30, 40, 50, 60, 70, 78, or 100 CAG triplet nucleotides. Such a cell is likely to exhibit nucleolar stress. In some cases, the composition itself binds the RNA containing the (CAG)$_n$ triplet nucleotide repeat. Such binding activity can act to sequester the RNA containing a (CAG)$_n$ triplet nucleotide repeat from disrupting cellular processes. For example, the composition can sequester the RNA containing a (CAG)$_n$ triplet nucleotide repeat from binding to nucleolin. In some cases, the cell expresses a nucleic acid encoding MJD$_{CAGn}$, or DsRed$_{CAGn}$, wherein each n is independently selected from about 10, 20, 30, 40, 50, 60, 70, 78, and 100. In some cases, the cell is from, or in, a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

Methods for treating a polyQ disease also include contacting a cell that expresses a peptide containing a polyQ amino acid sequence include the steps of contacting the cell with an effective amount of a composition that reduces polyQ-mediated cytotoxicity. In some cases, the composition itself binds the peptide containing the polyQ sequence. Such binding activity can act to sequester the polyQ peptide from disrupting cellular processes. For example, the composition can sequester the polyQ peptide from forming intracellular aggregates. In some cases, the cell expresses a nucleic acid encoding $MJD_{CAGn}$, $MJD_{CAA/Gn}$, or $MJD_{CAG/An}$, wherein each n is independently selected from about 10, 20, 30, 40, 50, 60, 70, 78, and 100. In some cases, the cell is from, or in, a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

IV. Pharmaceutical Compositions and Administration

The present invention also provides pharmaceutical compositions or physiological compositions comprising an effective amount of one or more polypeptides comprising an NCL RRM domain such as P3L and its structurally similar compounds or derivatives. Use of the compositions can be in both prophylactic and therapeutic applications for the treatment and prevention of a polyQ disease. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal administration. The preferred routes of administering the pharmaceutical compositions are intravenous or intraperitoneal delivery to a patient in need thereof (e.g., a human patient who is diagnosed of or is at risk of developing a polyQ disease) at doses of about 10-100,000 mg, 100-10,000 mg, 50-5,000 mg, 100, 200, 250, or 500 mg of each of the polypeptide for a 70 kg adult human per day or every other day. Some exemplary doses and administration frequencies include about 1, 2, 3, 4, 5, 6, 7, 8, 9, 10, 20, 30, 40, 50, 60, 70, 80, 90, or 100 mg/kg patient body weight for each polypeptide in each administration. Typically one or more polypeptides are administered to the patient either on once per day or per two-day basis. If more than one is administered, they can be administered at the same time or at separate times while all within the same general time frame. The polypeptide therapeutics may be administered in a single pharmaceutical composition or they may be in multiple separate compositions. Similarly, these polypeptides may be administered at the same time, or they may be administered on different days but all in close proximity to each other's administration, e.g., one administered on day 1 and other or others administered on day 2, such that the combined effects of these small molecules being co-administered are obtained. The appropriate dose may be administered in a single daily/bi-daily (once every other day) dose or as divided doses presented at appropriate intervals, for example as two, three, four, or more subdoses per day, or one dose every two, three, four, or five days.

For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., P3L and/or its derivatives. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., P3L and/or its derivatives). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of a polypeptide comprising an NCL RRM domain such as P3L and/or its derivatives with encapsulating material as a carrier providing a capsule in which the small molecule (with or without other carriers) is surrounded by the carrier, such that the carrier is thus in association with the small molecule or the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., P3L and/or its derivatives) or sterile solutions of the active component in solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., P3L and/or its derivatives) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between about 3 and about 11, more preferably from about 5 to about 9, and most preferably from about 7 to about 8.

The pharmaceutical compositions one or more polypeptides comprising an NCL RRM domain such as P3L and/or its derivatives can be administered to a patient who have received a diagnosis of a polyQ disease or is at risk of developing such a disease at a later time in an amount sufficient to prevent, eliminate, reverse, or at least partially slow or arrest the symptoms of polyQ disease such as any of the clinical symptoms of the cytotoxicity related to, caused by, or enhanced by expanded CAG-repeat RNA or polyQ polypeptide. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 1 mg to about 1000 mg per kg patient body weight, or about 5-500 mg/kg, about 10-100 mg/kg, about 20-50 mg/kg, e.g., about 10, 20, 25, 30, 40, 50, or 80, 100, 150, 200, or 300 mg/kg body weight for each small molecule therapeutic agent in each administration.

Single or multiple administrations of the compositions can be carried out with dose levels and pattern being selected by the treating physician. In any event, the pharmaceutical formulations should provide a quantity of a polypeptide comprising an NCL RRM domain such as P3L and/or its derivatives sufficient to effectively inhibit the undesired symptoms in the patient relating to expanded CAG-repeat RNA or polyQ polypeptide mediated cytotoxicity. Typically, the administration lasts at least 1, 2, 3, 4, 6, 8, 10, or 12 weeks and for as long as needed such as 6 months, 1, 2, 3, 4, 5, or 10, 15, 20 years on a daily, twice a day, bi-daily (once every other day), or weekly schedule.

While other active ingredient are generally not necessary to be co-administered to a recipient with the polypeptide therapeutics such as P3L and/or its derivatives in order to treat a patient suffering from or at risk of polyQ disease, it is optional that one or more additional therapeutically effective compounds may be co-administered along with the polypeptide(s), either in the same pharmaceutical composition(s) with the polypeptide(s) or in a separate pharmaceutical composition. For description of other therapeutic ingredients, see, e.g., U.S. Patent Application Publication No. 2014/0357578.

V. Kits

The invention also provides kits for treating a polyQ disease according to the method of the present invention. The kits typically include a first container that contains a pharmaceutical composition comprising a polypeptide comprising an NCL RRM domain that is therapeutically effective to ameliorate the symptoms of a polyQ disease, such as P3L or any one of its derivatives possessing a similar biological activity (e.g., capable of inhibiting cytotoxicity induced by expanded CAG-repeat RNA), optionally with an additional container that contains a pharmaceutical composition comprising another therapeutically effective compound for ameliorating the symptoms of a polyQ disease, such as another, different polypeptide or polynucleotide therapeutic agent including those described in U.S. Patent Application Publication No. 2014/0357578, or any one of the known polyQ protein toxicity inhibitors such as P42, QBP1, and Congo red. In some variations of the kits, a single container may contain a pharmaceutical composition comprising two or more of compounds effective for treating a polyQ disease such as polypeptide P3L and its derivatives, those described in U.S. Patent Application Publication No. 2014/0357578, as well as inhibitors of toxicity induced by polyQ proteins. The kits may further include informational material providing instructions on how to dispense the pharmaceutical composition(s), including description of the type of patients who may be treated (e.g., human patients who have received a diagnosis of a polyQ disease or have been deemed as risk of developing a polyQ disease, e.g., due to a strong propensity indicated by family history), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Introduction

Polyglutamine (PolyQ) diseases, including Machado Joseph Disease (MJD), represent a group of dominantly inherited progressive neurodegenerative diseases[1]. These diseases are caused by genomic CAG trinucleotide repeat expansion disease gene transcription and protein translation. Two primary toxic species—mRNA containing expanded CAG repeats and protein carrying an expanded polyQ domain—are produced in the neurons. These two mutant biomolecules induce neurotoxicity through multiple pathogenic pathways that lead to neurodegeneration[2-4].

Traditionally, the pathogenesis of polyQ diseases toxicity is ascribed to the misfolding and aggregation of expanded polyQ stretch-containing disease protein-induced neurodegeneration[5]. Different kinds of polyQ protein toxicity inhibitors, such as peptidylic inhibitor P42[6], QBP1[7], as well as the small molecular inhibitor Congo red[8], have been reported to be effective in both in vitro and in vivo models. However, few inhibitors have been found to targeting expanded CAG RNA toxicity. Although D6, a small molecule, has been reported to inhibit RNA toxicity in polyQ disease in vitro, it is yet to be tested in vivo'.

Our group previously demonstrated that the expanded CAG-repeat RNA could lead to nucleolar stress and eventually cause neurodegeneration in polyQ disease[10]. Transcription of expanded CAG RNA recruited the RNA/DNA binding protein nucleolin (NCL), and this RNA-protein interaction led to UCE hypermethylation and down-regulation of rRNA transcription, which ultimately triggered nucleolar stress-induced apoptosis[10]. Based on this mechanistic study, we previously developed a 13-amino acid peptide (DGKSKGIAYIEFK, SEQ ID NO:2), P3, which could inhibit the NCL-expanded CAG RNA interaction and suppress RNA toxicity in polyQ diseases. The peptide P3 was designed based on the structure of RRM2 of nucleolin and contains a RNP1 motif. Structural prediction of P3 suggests that the peptide mostly adopts coil conformation, which is believed to be relatively unstable. This prompted us to develop a more stable and potent peptidylic inhibitor for targeting RNA toxicity in polyQ disease.

Results

To reduce entropic loss upon binding of the flexible P3 to RNA, a longer peptide P3L was designed based on the NMR structure of nucleolin RRM2 (PDB ID=2KRR.PDB). P3L (AEIRLVSKDGKSKGIAYIEFK, SEQ ID NO:1) is a 21-amino acid long peptide comprises the sequence of P3 (DGKSKGIAYIEFK, SEQ ID NO:2) and an additional 8 amino acids at the N-terminus. The additional amino acids interact with the P3 residues to form a β-hairpin in the structure of nucleolin RRM2 and it is predicted that the P3L peptide also adopts a β-hairpin structure. Due to its more stable structure, it is expected that P3L may have improved binding to expanded CAG RNA due to lowered entropic loss.

Figure 2:
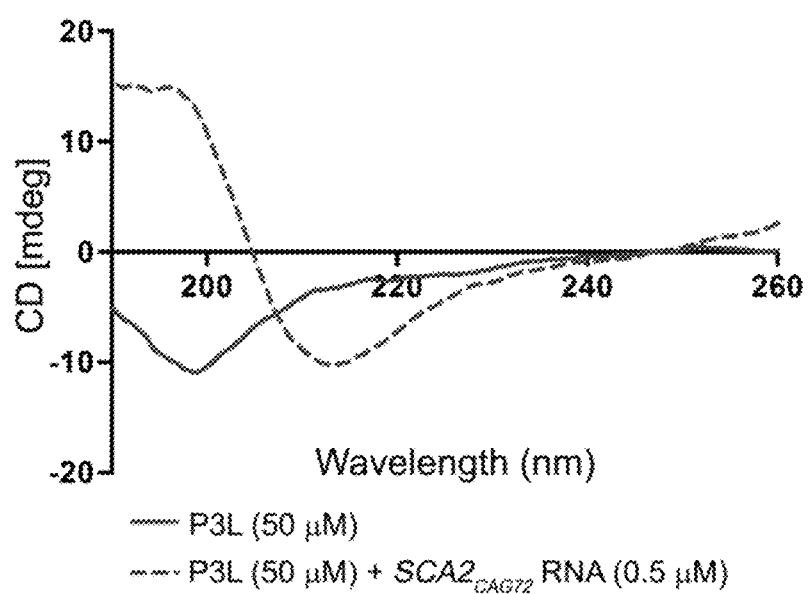
FIG. 2: Structural change of P3L upon interacting with $SCA2_{CAG72}$ RNA. Solid line shows far-UV CD spectrum of P3L measured at 25° C. in binding buffer (20 mM MOPS, pH 7.0; 300 mM NaCl). Dotted line shows CD spectrum of P3L in the presence of $SCA2_{CAG72}$ RNA measured at 25° C. in binding buffer (20 mM MOPS, pH 7.0; 300 mM NaCl). Data were calculated by subtracting CD spectrum of buffer alone or $SCA2_{CAG72}$ RNA.

Based on circular dichroism spectroscopy[11], P3L demonstrated a β-sheet/random coil structure. Upon the addition of expanded SCA2$_{CAG72}$ RNA, P3L showed a transition from a random coil structure to an α-helix structure (minimum at 208 nm and maximum at 192 nm), reflecting an interaction between P3L and SCA2$_{CAG72}$ RNA (FIG. 2).

Figure 3:
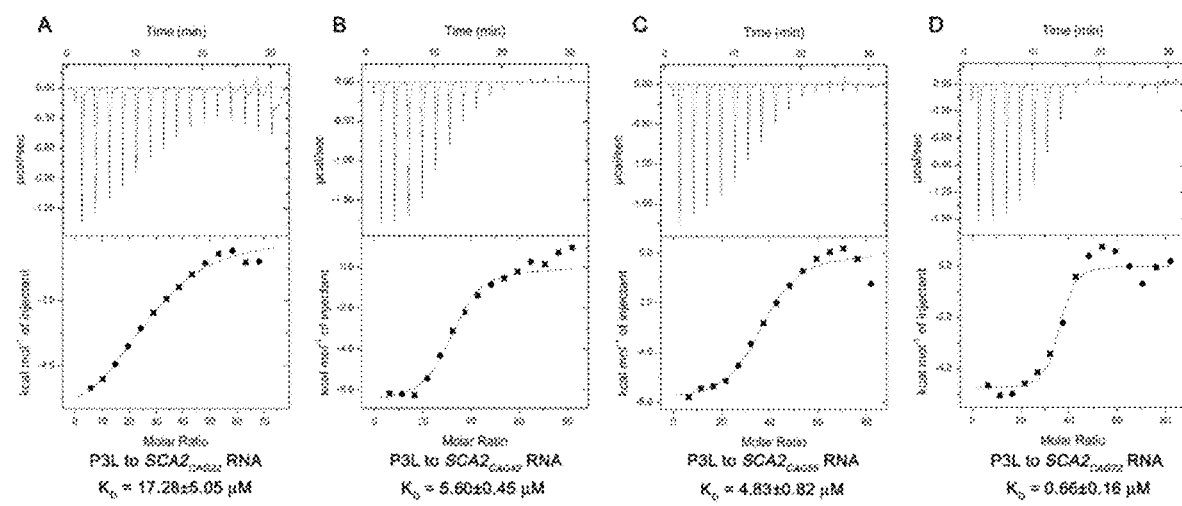
FIG. 3: P3L directly interacted with CAG repeat-containing RNAs. iTC study of the binding of synthetic P3L peptide (2 mM) to CAG RNA (4 μM) in vitro transcribed from (A) pcDNA3.1-$SCA2_{CAG22}$, (B) pcDNA3.1-$SCA2_{CAG42}$, (C) pcDNA3.1-$SCA2_{CAG55}$ and (D) pcDNA3.1-$SCA2_{CAG72}$. The top panel shows the raw thermograms and the bottom panel shows the binding isotherms fitted to a single-site model.

We hypothesized that P3L can prevent interaction of NCL and expanded CAG RNA by directly binding to expanded CAG RNA. Hence, we performed isothermal titration calorimetry (iTC)[12, 13] to determine the RNA-binding property of P3L toward different lengths of CAG-repeat RNAs_EN-REF_21. Our data showed that P3L associated with unexpanded SCA2$_{CAG22}$ RNA with a K$_D$ value of 17.28±5.05 μM (FIG. 3A). This indicates that P3L bound more tightly with expanded SCA2$_{CAG42/55}$ RNA. The K$_D$ values of P3L toward SCA2$_{CAG42}$ and SCA2$_{CAG55}$ RNA were determined to be 5.60±0.45 and 4.83±0.82 respectively (FIGS. 3B&C). However, when compared to SCA2$_{CAG22/42/55}$ RNAs, P3L associated most tightly to expanded SCA2$_{CAG72}$ RNA with a K$_D$ value of 0.66±0.16 μM (FIG. 3D). These results indicated that P3L has a stronger interaction with long expanded CAG repeat RNA.

Cell-penetrating peptides (CPPs), such as TAT peptide, have been widely used as a vehicle to deliver therapeutics across the cell membrane[14], including the peptidylic inhibitors of polyQ protein toxicity QBP1[15] and httNT[16]. We previously demonstrated that TAT-P3 peptide suppressed neurodegeneration by inhibiting nucleolar stress in polyQ disease. Here, we chose pre-45s rRNA expression level as a biomarker to investigate if TAT-P3L also works on the nucleolar stress pathway. Our data showed that TAT-P3L could restore the pre-45s rRNA transcription level in expanded CAG-repeat RNA-expressing HEK293 cells in a concentration-dependent manner (FIG. 4A). We further demonstrated that TAT-P3L could also restore pre-rRNA expression level in DsRed$_{CAG100}$ Drosophila model, an in vivo model which only manifested CAG-repeat RNA toxicity (FIG. 4B). Collectively, these data indicate that TAT-P3L could mitigate the expanded CAG-repeat RNA toxicity in the nucleolar stress pathway.

Figure 5:
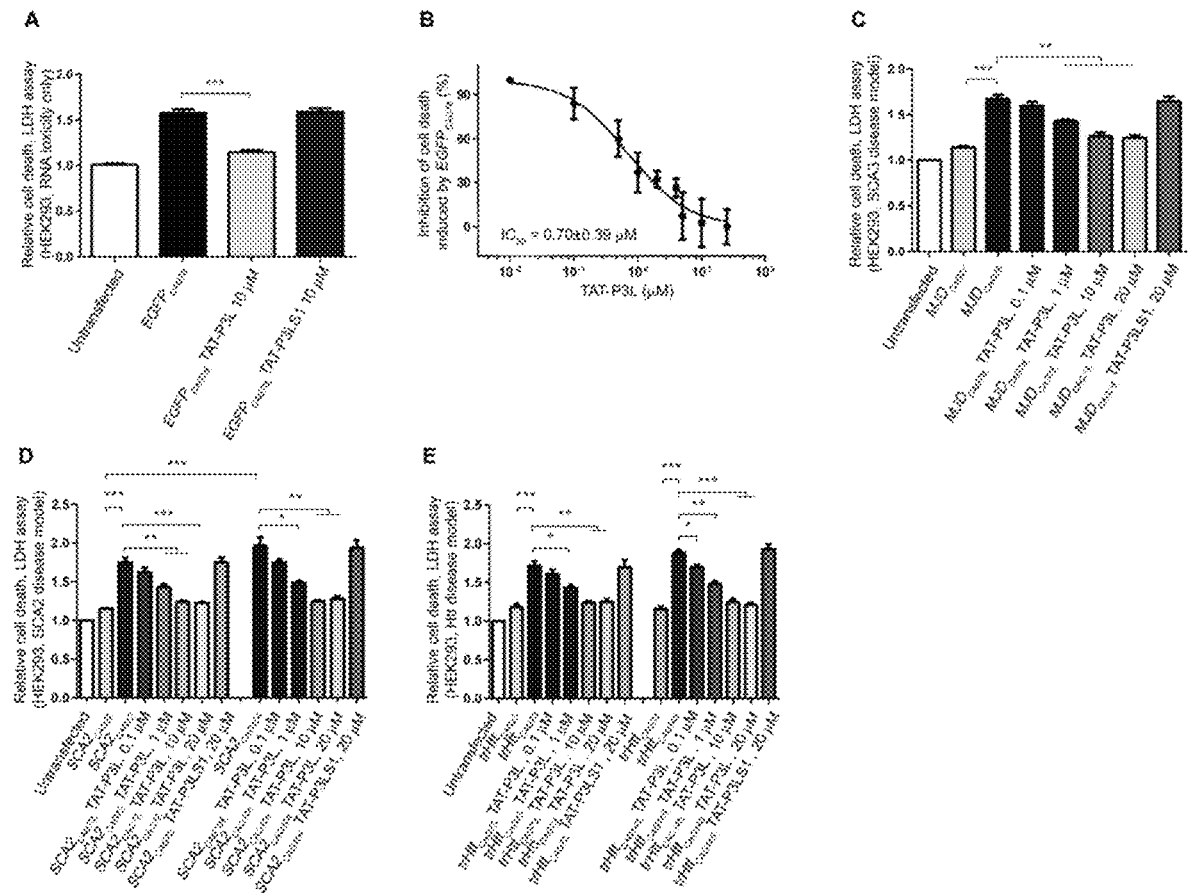
FIG. 5: TAT-P3L inhibited expanded CAG-repeat RNA-induced cell death in polyQ disease. (A) P3L inhibited cell death in $EGFP_{CAG78}$ (only RNA toxicity)-expressing HEK293 cells. (B) $IC_{50}$ value of P3L, calculated based on concentration-dependently inhibition of cell death in $EGFP_{CAG78}$ (only RNA toxicity)-expressing HEK293 cells. $IC_{50}$ represents the concentration of P3L that reduced LDH enzyme activity by 50% when compared to the untreated control group. (C-E) P3L caused a significant but not fully inhibition in cell death in $MJD_{CAG78}$ (C), $SCA2_{CAG72/104}$ (D) and $trHtt_{CAG72/145}$ (E)-expressing HEK293. All of these models exhibit both CAG-repeat RNA and polyQ protein expression.

We next investigated if TAT-P3L could suppress neurotoxicity in polyQ disease cell model. By means of the lactate dehydrogenase (LDH) cytotoxicity assay[17], we found that TAT-P3L but not TAT-P3L-S1, a scrambled control of TAT-P3L, significantly suppressed EGFP$_{CAG78}$ RNA-induced cell death (FIG. 5A). The calculated half maximal inhibitory concentration (IC$_{50}$) value of TAT-P3L in inhibiting expanded CAG-repeat RNA-induced cell death was 0.70±0.39 μM (FIG. 5B). In order to evaluate the activity of TAT-P3L in different polyQ diseases, we then tested if TAT-P3L could inhibit cell death in MJD$_{CAG78}$ (MJD disease model), SCA2$_{CAG72/104}$ (Spinocerebellar Ataxia Type 2 (SCA2) disease model) as well as trHtt$_{CAG72/145}$ (Huntington (Htt) disease model)-expressing HEK293 cells. Our data demonstrated that TAT-P3L caused a concentration-dependent suppression in cell death in MJD (FIG. 5C), SCA2 (FIG. 5D) and Htt (FIG. 5E) disease cell models.

Figure 6:
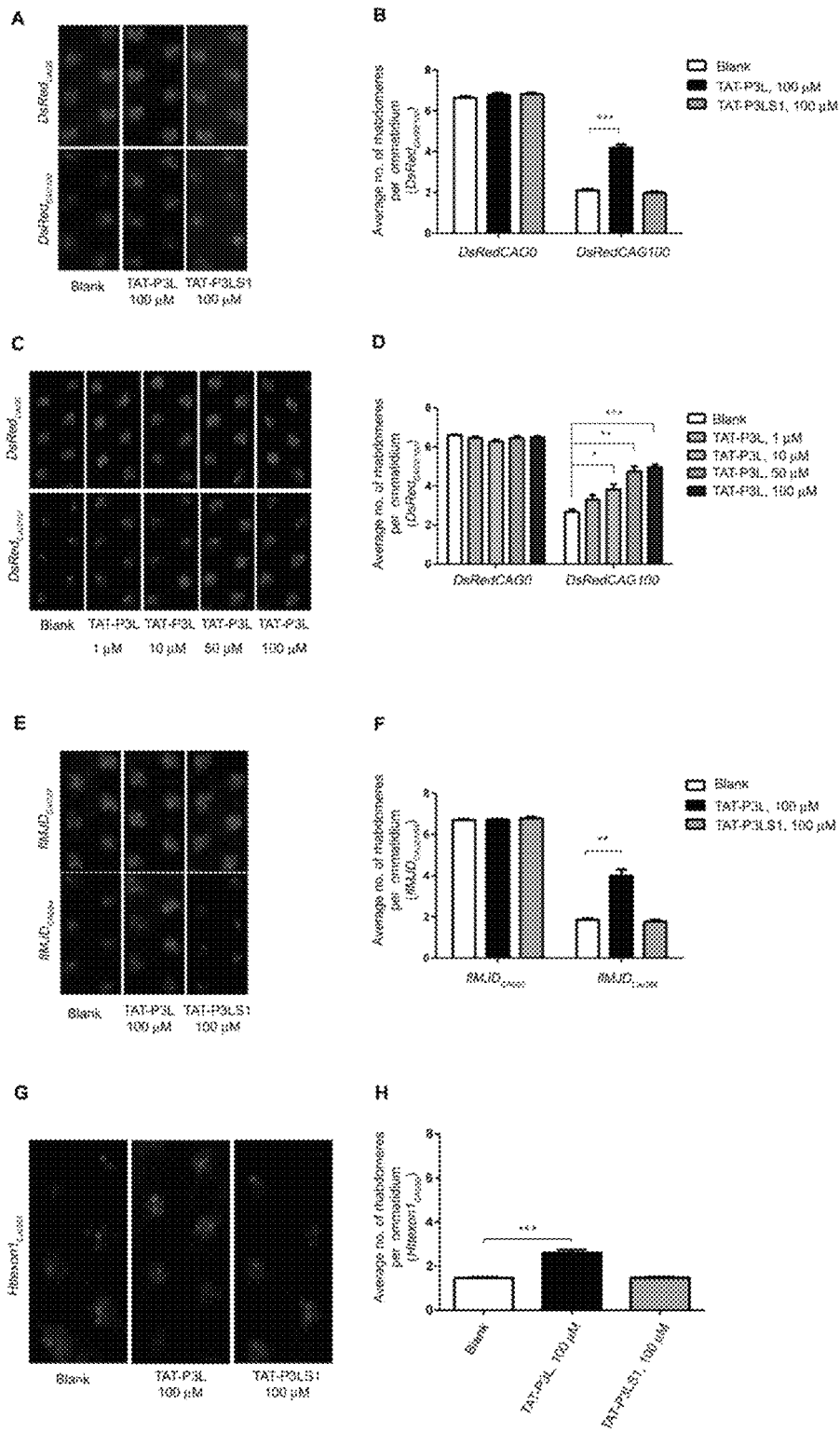
FIG. 6: TAT-P3L suppressed retinal degeneration in different polyQ disease models. (A) TAT-P3L but not TAT-P3L-S1 suppressed the neurodegeneration in $DsRed_{CAG100}$ flies which only possessed RNA toxicity. (B) Statistical analysis of (A). (C) TAT-P3L suppressed the neurodegeneration in $DsRed_{CAG100}$ flies in a concentration-dependent manner. (D) Statistical analysis of (C). (E) TAT-P3L but not TAT-P3L-S1 inhibited the neurodegeneration in $flMJD_{CAG84}$ flies which expressing both CAG-repeat RNA and MJD disease protein. (F) Statistical analysis of (E). (G) TAT-P3L but not TAT-P3L-S1 inhibited the neurodegeneration in $Httexon1_{CAG93}$ flies which expressing both CAG-repeat RNA and Htt disease protein. (H) Statistical analysis of (G).

Besides in vitro study, we also investigated the effect of TAT-P3L on inhibiting neurodegeneration in a DsRed$_{CAG100}$ fly model[18], one of the in vivo models that only expresses CAG-repeat RNA but not polyQ protein. We previously showed that expression of expanded CAG-repeat RNA or/and polyQ disease protein caused severe retinal degeneration, which can be quantified by the pseudopupil assay[19]. By using this assay, we found that treatment of TAT-P3L but not TAT-P3L-S1 elicited a concentration-dependent inhibition of neurodegeneration in DsRed$_{CAG100}$ flies (FIG. 6A-D). We further demonstrated that treatment of TAT-P3L but not TAT-P3L-S1 suppressed retinal degeneration flMJD$_{CAG84}$ (MJD disease model; FIGS. 6E&F) and Httexon1$_{CAG93}$ (Htt disease model) flies (FIGS. 6G&H).

Figure 7:
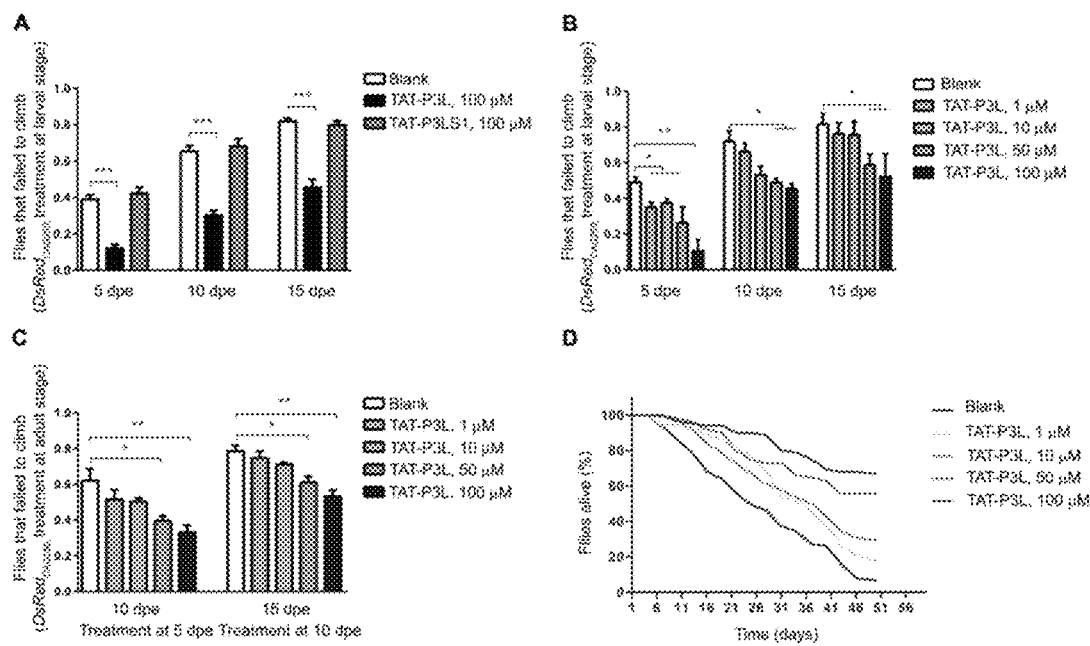
FIG. 7: TAT-P3L improved climbing ability and extended lifespan of $DsRed_{CAG250}$ flies. (A) Treatment of TAT-P3L but not TAT-P3L-S1 at larval stage rescued the climbing defect in $DsRed_{CAG250}$ flies (only RNA toxicity). (B) Treatment of TAT-P3L at larval stage improved climbing ability of $DsRed_{CAG250}$ flies in a concentration-dependent manner. (C) Treatment of TAT-P3L at adult stage improved climbing ability of $DsRed_{CAG250}$ flies in a concentration-dependent manner. (D) Treatment of TAT-P3L concentration-dependently extended the lifespan of $DsRed_{CAG250}$ flies.

In addition to pseudopupil assay, climbing ability assay and lifespan analysis have also been demonstrated as effective tools for evaluating new therapeutic drugs for neurodegenerative diseases[20, 21]. Flies expressing DsRed$_{CAG250}$ globally in neurons using elav-GAL4 demonstrated progressive loss of climbing ability and lethality when compared to control flies DsRed$_{CAG0}$[18]. Thus, we used this model that only expresses CAG-repeat RNA to further investigate the suppressive effect of TAT-P3L in vivo. Our data clearly showed that larval treatment of TAT-P3L but not TAT-P3L-S1 at ameliorated the climbing ability of 5, 10 and 15 day-old adult DsRed$_{CAG250}$ flies in a dose-dependent manner (FIGS. 7A&B). This implies that TAT-P3L when administered at the larval stage could defer the onset of degenerative phenotype in DsRed$_{CAG250}$ flies. We next investigated if the treatment would still remain effective if TAT-P3L was given after DsRed$_{CAG250}$ flies already showed degeneration. Our results showed that such late adult stage TAT-P3L treatment could also cause a dose-dependent improvement of the climbing ability of DsRed$_{CAG250}$ flies (FIG. 7C). This highlights the treatment effectiveness of TAT-P3L in symptomatic animals. Further, we showed that TAT-P3L extended the lifespan of DsRed$_{CAG250}$ flies in a dose-dependent manner. All the above data clearly illustrate the therapeutic effect of TAT-P3L in polyQ disease in vivo (FIG. 7D).

Figure 8:
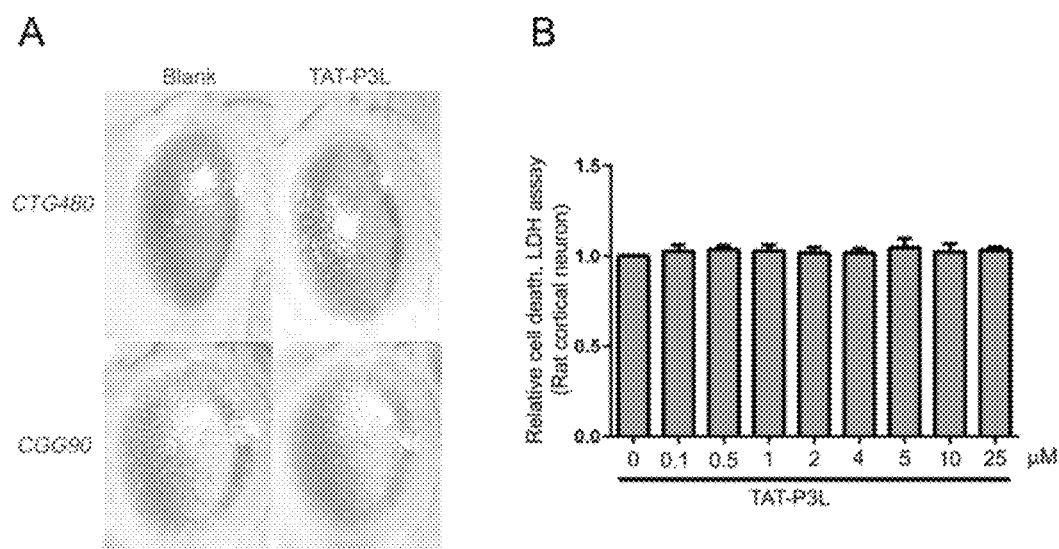
FIG. 8: (A) TAT-P3L did not suppress the neurodegeneration in CTG480 & CGG90 flies. (B) TAT-P3L did not show dominant toxic effect on primary rat cortical neurons.
Figure 9:
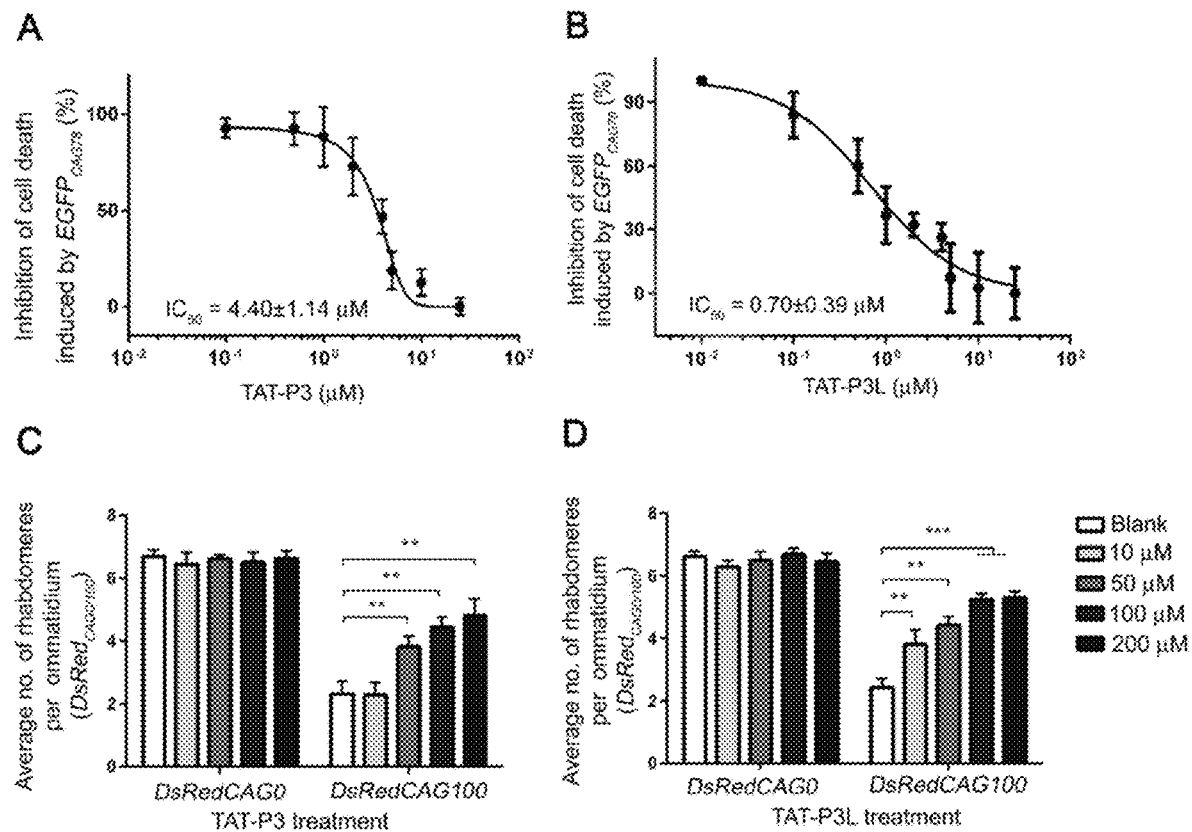
FIG. 9: P3L suppressed CAG-repeat RNA-induced cell death and neurodegeneration more effectively than P3. (A-B) The IC50 values of TAT-P3 (A) and TAT-P3L (B), calculated based on concentration-dependently inhibition of cell death in EGFPCAG78 (only RNA toxicity)-expressing HEK293 cells, were 4.4+/−1.14 μM and 0.7+/−0.39 μM respectively. IC50 represents the concentration of TAT-P3/ TAT-P3L that reduced LDH enzyme activity by 50% when compared to the untreated control group. (C-D) Determination of the effect of TAT-P3 and TAT-P3L on neurodegeneration in DsRedCAG100 flies using pseudopupil assay. At 50 uM concentration, TAT-P3L (D) suppressed neurodegeneration more effectively than TAT-P3 (C) in DsRedCAG100 flies.

Other disease fly models, including CTG480 (Myotonic dystrophy 1)[14] and CGG90 (Fragile X syndrome)[15] were employed to determine the specificity of TAT-P3L on trinucleotide repeat expansion RNA toxicity. Consistent with previous reports, both the CTG480 and CGG90 models showed degenerative phenotypes (FIG. 8A). The TAT-P3L treatment of these flies did not mitigate the phenotypes (FIG. 8A), suggesting that the TAT-P3L is a specific inhibitor toward expanded CAG-repeat RNA-mediated toxicity in vivo. Further, cytotoxicity test on primary rat cortical neurons showed that the viability of the wild-type primary neurons was not compromised when they were treated with up to 25 μM of TAT-P3L (FIG. 8B). This clearly indicates that TAT-P3L per se does not elicit observable dominant toxic effect on mammalian neurons at micromolar concentrations.

Materials and Methods

Circular Dichroism Spectroscopy Measurements of P3L

The circular dichroism (CD) spectra for the P3L were obtained in 20 mM MOPS pH 7.0 with 300 mM NaCl in the absence or presence of SCA2$_{CAG72}$ RNA. The JASCO J-810 parameters were set to the following: scan range 190-260 nm, scan speed 20 nm/min, 1 s response time, 1 nm bandwidth and 3 acquisitions. All CD spectra were obtained at 25° C. Data were calculated by subtracting CD spectra of buffer alone or SCA2$_{CAG72}$ RNA.

Isothermal Titration Calorimetry (ITC) Binding Assay

Experiments were carried out using a MicroCal iTC200 isothermal titration calorimeter (GE Healthcare) at 25° C. Data were analyzed using the Origin® scientific plotting software version 7 (Microcal Software Inc.). All RNAs and peptides were dissolved in binding buffer (20 mM MOPS, pH 7.0; 300 mM NaCl)[13]. The concentration of RNA was estimated with appropriate extinction coefficients at 260 nm on a Nanodrop 2000 (Thermo Scientific). P3L (2 mM) was titrated to in vitro transcribed SCA2$_{CAG22/42/55/72}$ RNA (4 μM). A reference power of 8 μcal/s was used with an initial 0.5 μl of injection of peptide followed by 2 μl for all subsequent titrations points with a 60 s initial equilibrium delay and 120 s pause between injections. The samples were stirred at a speed of 1,000 r.p.m. throughout the experiment. The thermal titration data were fitted to the 'one binding site model' to determine the dissociation constant ($K_D$).

RNA Extraction, Reverse Transcription and Real-Time PCR

RNA was extracted from cells by Trizol reagent (Life Technologies), and 1 μg of purified RNA was then used for reverse-transcription using the ImPromII™ Reverse Transcription System (Promega). Random hexamer (Roche) was used as primers in reverse transcription. Taqman gene expression assays were performed on an ABI 7500 Real-time PCR system and data were analyzed as previously described[10]. The following probes were used: pre-45s rRNA (Assay ID: AILJIZM), actin (Assay ID: Hs99999903_m1), pre-rRNA (Assay ID: AIMSG5U) and GAPDH for *Drosophila* (Assay ID: Dm01841186).

Lactate Dehydrogenase (LDH) Cytotoxicity Assay

Human embryonic kidney 293 cells were seeded on a 24-well plate at a density of $0.5 \times 10^5$, and pcDNA3.1-MJD$_{CAG27/78}$ or, pEGFP$_{CAG78}$ or, pcDNA3.1-SCA2$_{CAG22/72/104}$ or pEGFP-trHtt$_{CAG23/73/145}$ construct was used to transfect the cells. Lactate dehydrogenase enzyme activity in the cell culture medium was measured 72 h post-transfection and drugs treatment using the Cytotox 96 non-radioactive cytotoxicity assay (Promega).

Peptide Feeding, Pseudopupil Assay, External Eye Assay, Climbing Ability Assay, and Lifespan Analysis For pseudopupil assay, flies were raised at 21.5° C. on cornmeal medium supplemented with dry yeast. For climbing ability assay, lifespan analysis as well as external eye assay, flies were raised at 25° C. on cornmeal medium supplemented with dry yeast. We usually feed flies at larval stage unless otherwise indicated. For larval stage treatment, third instar larvae were fed with different concentration of TAT-P3L dissolved in 2% sucrose solution for 2 h and then continued to culture in standard fly food. For adult stage treatment, 5 or 10 day-old adult flies were starved for 8 h and then fed with different concentrations of TAT-P3L dissolved in 2% sucrose solution overnight. After treatment, flies were cultured in standard fly food.

Pseudopupil assay[18] was performed on 12 day-old adult flies except for Httexon1$_{CAG93}$ which 1 day-old adult flies were used for the assay. Images were captured by SPOT Insight CCD camera controlled by the SPOT Advanced software (Diagnostic instruments Inc.). External eye assay was performed on 1 day-old adult of CTG480 flies and 2 day-old adult of CGG90 flies using an Olympus SZX-12 stereomicroscope. Eye images were captured using a SPOT Insight CCD camera (Diagnostic instruments Inc.). Fly climbing ability was analyzed by negative geotaxis. Groups of ~15 flies of same gender were anesthetized and placed in a vertical plastic column. After 1 h recovery, flies were banged to the bottom, and then scored for climbing ability as the percentage of flies remaining at the bottom (<2 cm) at 25s. Three trials were performed at 3 min intervals in each experiment. 80-120 flies were tested per treatment for climbing ability assay. Lifespan analysis was performed as previously described[22]. 120-150 flies were tested per treatment for lifespan analysis.

All patents, patent applications, and other publications, including GenBank Accession Numbers, cited in this application are incorporated by reference in the entirety for all purposes.

REFERENCES

1. Orr, H. T. & Zoghbi, H. Y. Trinucleotide repeat disorders. *Annu. Rev. Neurosci.* 30, 575-621 (2007).
2. Fiszer, A. & Krzyzosiak, W. J. RNA toxicity in polyglutamine disorders: concepts, models, and progress of research. *J. Mol. Med.* (Berl) 91, 683-691 (2013).
3. Nalavade, R., Griesche, N., Ryan, D. P., Hildebrand, S. & Krauss, S. Mechanisms of RNA-induced toxicity in CAG repeat disorders. *Cell. Death Dis.* 4, e752 (2013).
4. Williams, A. J. & Paulson, H. L. Polyglutamine neurodegeneration: protein misfolding revisited. *Trends Neurosci.* 31, 521-528 (2008).
5. Takahashi, T., Katada, S. & Onodera, O. Polyglutamine diseases: where does toxicity come from? what is toxicity? where are we going? *J. Mol. Cell. Biol.* 2, 180-191 (2010).
6. Arribat, Y. et al. A huntingtin peptide inhibits polyQ-huntingtin associated defects. *PLoS One* 8, e68775 (2013).
7. Nagai, Y. et al. Inhibition of polyglutamine protein aggregation and cell death by novel peptides identified by phage display screening. *J. Biol. Chem.* 275, 10437-10442 (2000).
8. Sanchez, I., Mahlke, C. & Yuan, J. Pivotal role of oligomerization in expanded polyglutamine neurodegenerative disorders. *Nature* 421, 373-379 (2003).
9. Kumar, A. et al. Chemical correction of pre-mRNA splicing defects associated with sequestration of muscleblind-like 1 protein by expanded r(CAG)-containing transcripts. *ACS Chem. Biol.* 7, 496-505 (2012).
10. Tsoi, H., Lau, T. C., Tsang, S. Y., Lau, K. F. & Chan, H. Y. CAG expansion induces nucleolar stress in polyglutamine diseases. *Proc. Natl. Acad. Sci. U.S.A* 109, 13428-13433 (2012).
11. Raussens, V., Ruysschaert, J. M. & Goormaghtigh, E. Protein concentration is not an absolute prerequisite for the determination of secondary structure from circular dichroism spectra: a new scaling method. *Anal. Biochem.* 319, 114-121 (2003).
12. Li, M. et al. Selection of peptides that target the aminoacyl-tRNA site of bacterial 16S ribosomal RNA. *Biochemistry* 48, 8299-8311 (2009).
13. Wong, C. H. et al. Targeting toxic RNAs that cause myotonic dystrophy type 1 (DM1) with a bisamidinium inhibitor. *J. Am. Chem. Soc.* 136, 6355-6361 (2014).
14. Koren, E. & Torchilin, V. P. Cell-penetrating peptides: breaking through to the other side. *Trends Mol. Med.* 18, 385-393 (2012).
15. Popiel, H. A., Nagai, Y., Fujikake, N. & Toda, T. Protein transduction domain-mediated delivery of QBP1 suppresses polyglutamine-induced neurodegeneration in vivo. *Mol. Ther.* 15, 303-309 (2007).
16. Mishra, R. et al. Inhibiting the nucleation of amyloid structure in a huntingtin fragment by targeting alpha-helix-rich oligomeric intermediates. *J. Mol. Biol.* 415, 900-917 (2012).
17. Banez-Coronel, M. et al. A pathogenic mechanism in Huntington's disease involves small CAG-repeated RNAs with neurotoxic activity. *PLoS Genet.* 8, e1002481 (2012).
18. Li, L. B., Yu, Z., Teng, X. & Bonini, N. M. RNA toxicity is a component of ataxin-3 degeneration in *Drosophila*. *Nature* 453, 1107-1111 (2008).
19. Chan, W. M. et al. Expanded polyglutamine domain possesses nuclear export activity which modulates subcellular localization and toxicity of polyQ disease protein via exportin-1. *Hum. Mol. Genet.* 20, 1738-1750 (2011).
20. Shaltiel-Karyo, R. et al. A novel, sensitive assay for behavioral defects in Parkinson's disease model *Drosophila. Parkinson Dis.* 2012, 697564 (2012).

21. Muqit, M. M. & Feany, M. B. Modelling neurodegenerative diseases in *Drosophila*: a fruitful approach? *Nat. Rev. Neurosci.* 3, 237-243 (2002).

22. Linford, N. J., Bilgir, C., Ro, J. & Pletcher, S. D. Measurement of lifespan in *Drosophila melanogaster. J. Vis. Exp.* (71). pii: 50068. doi, 10.3791/50068 (2013).

What is claimed is:

1. An isolated polypeptide consisting of (1) a fragment of the nucleolin (NCL) protein consisting of the amino acid sequence of SEQ ID NO:1; and (2) one or more heterologous amino acid sequences located at the N-terminus and/or C-terminus of the polypeptide, wherein the polypeptide has less than 100 amino acids.

2. The polypeptide of claim 1, wherein the one or more heterologous amino acid sequences is a trans-activating transcriptional activator (TAT) peptide.

3. The polypeptide of claim 1, wherein the polypeptide has less than 50 amino acids in length.

4. The polypeptide of claim 1, consisting of the amino acid sequence of SEQ ID NO:1 and a TAT peptide at the N-terminus of the polypeptide.

5. A composition comprising the polypeptide of claim 1 and a physiologically acceptable excipient.

6. The composition of claim 5, wherein the polypeptide consists of the amino acid sequence of SEQ ID NO:1 and a TAT peptide at the N-terminus of the polypeptide.

7. The composition of claim 5, further comprising another therapeutic agent effective for reducing polyQ-mediated cytotoxicity.

8. The composition of claim 7, wherein the agent is a polyQ protein toxicity inhibitor.

9. The composition of claim 8, wherein the polyQ protein toxicity inhibitor is P42 (SEQ ID NO:7) or polyQ-binding peptide 1 (QBP1, SEQ ID NO:6).

10. A kit for reducing polyQ-mediated cytotoxicity, comprising a container containing a pharmaceutical composition of claim 5.

11. A method for reducing polyQ-mediated cytotoxicity in a subject who has been diagnosed with a polyQ disease, comprising administering to the subject an effective amount of the polypeptide of claim 1.

12. The method of claim 11, wherein the polypeptide consists of the amino acid sequence of SEQ ID NO:1 and a TAT peptide at the N-terminus of the polypeptide.

13. The method of claim 11, wherein another therapeutic agent effective for reducing polyQ-mediated cytotoxicity is co-administered to the subject.

14. The method of claim 13, wherein the agent is a polyQ protein toxicity inhibitor.

15. The method of claim 14, wherein the polyQ protein toxicity inhibitor is P42 or QBP1.

16. The method of claim 11, wherein the polypeptide is administered orally, intravenously, intramuscularly, intraperitoneally, or subcutaneously.

17. The method of claim 11, wherein the polypeptide is administered once daily, weekly, or monthly.

18. The method of claim 11, wherein about 1-11,000 mg, about 10-1,000 mg, about 10-100 mg, about 20-50 mg, or about 10, 20, 30, 40, or 50 mg of the polypeptide is administered each time to the subject per kg of the subject's body weight.

* * * * *